US012046336B2

(12) United States Patent
Osborn et al.

(10) Patent No.: US 12,046,336 B2
(45) Date of Patent: Jul. 23, 2024

(54) SECURE VERIFICATION OF MEDICAL STATUS USING A CONTACTLESS CARD

(71) Applicant: Capital One Services, LLC, McLean, VA (US)

(72) Inventors: Kevin Osborn, Newton, MA (US); Jeffrey Rule, Chevy Chase, MD (US)

(73) Assignee: Capital One Services, LLC, McLean, VA (US)

( * ) Notice: Subject to any disclaimer, the term of this patent is extended or adjusted under 35 U.S.C. 154(b) by 0 days.

(21) Appl. No.: 17/948,401

(22) Filed: Sep. 20, 2022

(65) Prior Publication Data

US 2023/0039938 A1     Feb. 9, 2023

Related U.S. Application Data

(63) Continuation of application No. 17/086,029, filed on Oct. 30, 2020, now Pat. No. 11,482,312.

(51) Int. Cl.
*G16H 10/65* (2018.01)
*G16H 50/30* (2018.01)
(Continued)

(52) U.S. Cl.
CPC ............ *G16H 10/65* (2018.01); *G16H 50/30* (2018.01); *H04L 9/0825* (2013.01); *H04L 9/3247* (2013.01); *H04L 2209/805* (2013.01)

(58) Field of Classification Search
CPC ...... G16H 10/65; G16H 50/30; H04L 9/0825; H04L 9/3247; H04L 2209/805
See application file for complete search history.

(56) References Cited

U.S. PATENT DOCUMENTS

| 2015/0199673 | A1* | 7/2015 | Savolainen | ........ G06Q 20/4012 705/72 |
| 2021/0326474 | A1* | 10/2021 | Sparks | .................... G06Q 10/10 |
| 2021/0358068 | A1* | 11/2021 | Boszczyk | ............ G06Q 50/265 |

OTHER PUBLICATIONS

M. Eisenstadt, M. Ramachandran, N. Chowdhury, A. Third, and J. Domingue, "COVID-19 Antibody Test/Vaccination Certification: There's an App for That," IEEE Open Journal of Engineering in Medicine and Biology, vol. 1, pp. 148-155, 2020, doi: 10.1109/OJEMB.2020.2999214 (Year: 2020).*

(Continued)

*Primary Examiner* — Robert A Sorey
*Assistant Examiner* — Kristine K Rapillo
(74) *Attorney, Agent, or Firm* — KDW Firm PLLC

(57) ABSTRACT

Systems, methods, articles of manufacture, and computer-readable media for verification of medical status using a contactless card. An application may receive a request specifying a subject and a medical condition. The application may receive a cryptogram from a contactless card. The application may receive a decryption result from a server and determine that the server decrypted the cryptogram. The application may receive, from the contactless card, a medical attestation, a digital signature of the medical attestation, and a public key of the digital signature. The application may decrypt the digital signature based on the public key of the digital signature and verify the medical attestation based on the decrypted digital signature. The application may determine, based on the verification of the medical attestation, that the subject is immune to the medical condition. The application may output a result that the subject is immune to the medical condition.

19 Claims, 14 Drawing Sheets

(51) Int. Cl.
*H04L 9/08* (2006.01)
*H04L 9/32* (2006.01)

(56) References Cited

OTHER PUBLICATIONS

Eisenstadt et al.,(M. Eisenstadt, M. Ramachandran, N. Chowdhury, A. Third, and J. Domingue, "COVID-19 Antibody Test/Vaccination Certification: There's an App for That," IEEE Open Journal of Engineering in Medicine and Biology, vol. 1, pp. 148-155 , 2020, doi: 10.1109/OJEMB.20 (Year: 2020).*

* cited by examiner

SECURE VERIFICATION OF MEDICAL STATUS USING A CONTACTLESS CARD

TECHNICAL FIELD

This application is a continuation of U.S. patent application Ser. No. 17/086,029, entitled "SECURE VERIFICATION OF MEDICAL STATUS USING A CONTACTLESS CARD" filed on Oct. 30, 2020. The contents of the aforementioned application are incorporated herein by reference in their entirety.

TECHNICAL FIELD

Embodiments disclosed herein generally relate to contactless cards, and more specifically, to secure verification of medical status using contactless cards.

BACKGROUND

Often, people must provide proof of a medical status, such as immunization, to a requesting entity. This requirement is exacerbated during a pandemic and thereafter. However, it is impractical for people to carry physical documentation. Furthermore, the authenticity of documentation of any type must be considered. Similarly, the privacy of each person must be preserved. Conventional solutions fail to address these and other considerations.

SUMMARY

Embodiments disclosed herein provide systems, methods, articles of manufacture, and computer-readable media for secure verification of medical status using a contactless card. In one example, an application may receive a request specifying a subject and a medical condition. The application may receive a cryptogram from a contactless card associated with an account of the subject. The application may receive a decryption result from a server and determine that the server decrypted the cryptogram. The application may receive, from the contactless card based on the decryption result, a medical attestation, a digital signature of the medical attestation, and a public key of the digital signature. The application may decrypt the digital signature based on the public key of the digital signature and verify the medical attestation based on the decrypted digital signature. The application may determine, based on the verification of the medical attestation, that the subject is immune to the medical condition. The application may output an attestation result specifying that the subject is immune to the medical condition.

DETAILED DESCRIPTION

Figure 1A:
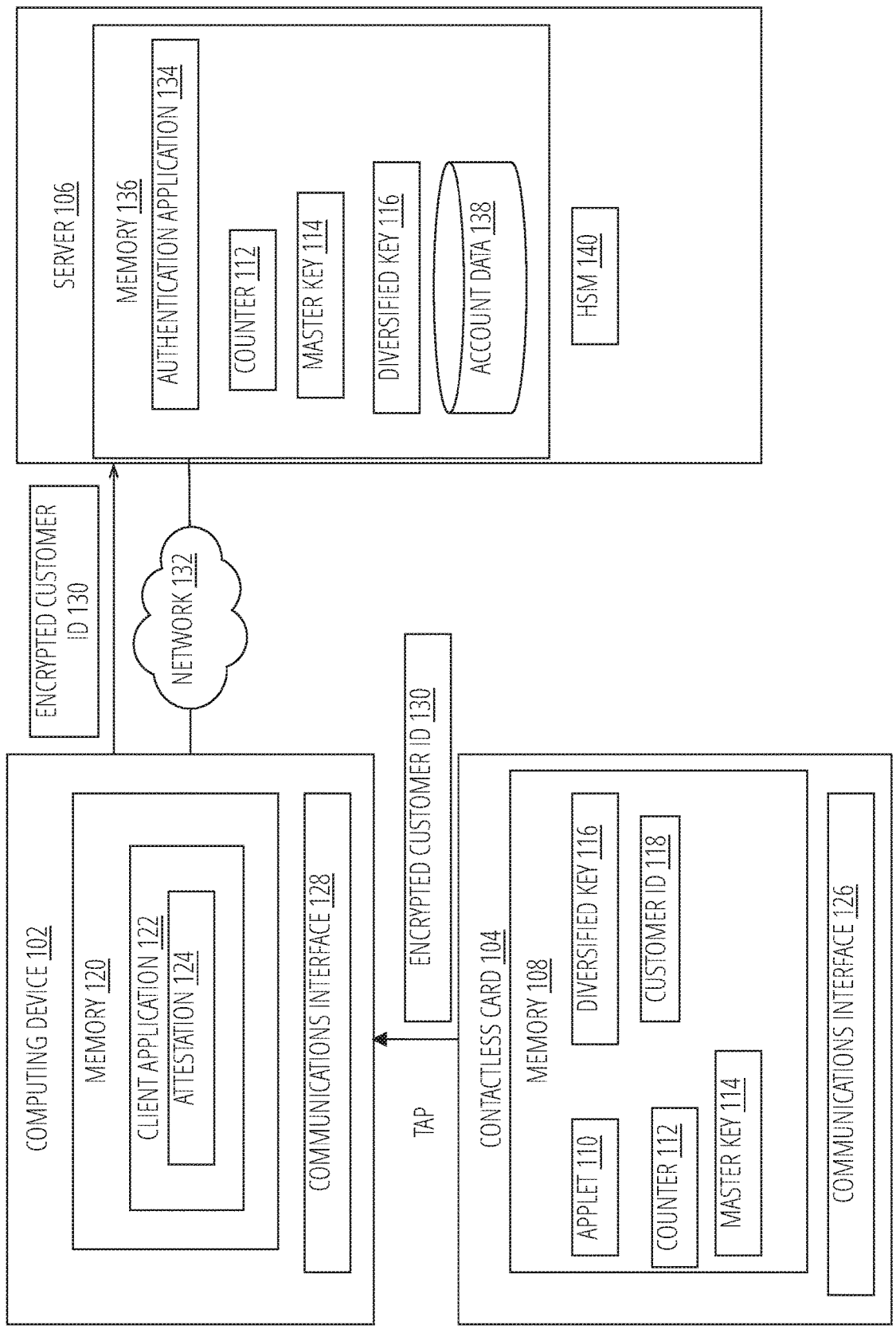
FIGS. 1A-1B illustrate embodiments of a system.

Embodiments disclosed herein provide techniques for secure verification of medical status using a contactless card. Generally, a contactless card may store a medical attestation. The medical attestation may relate to any health attribute of a person, such as immunization status, infection status, and the like. The medical attestation may be signed by a certified entity, such as a healthcare provider who administered a vaccine.

At a later time, the associated person may need to verify the medical attestation, e.g., prove that they have received an immunization. For example, the person may attempt to use public transit, and a terminal at the public transit station may request the proof of immunization. The person may tap their contactless card to the terminal, which causes the contactless card to generate a data package. The data package may include a dynamic cryptogram generated using key diversification. The terminal may transmit the cryptogram to an authentication server for decryption using key diversification. If the authentication server is able to decrypt the cryptogram, the authentication server may generally verify and/or validate the identity of the person. The authentication server may then transmit a decryption result to the terminal, e.g., whether the cryptogram was decrypted and/or the identity of the person is verified.

If decryption result indicates authentication server decrypted the cryptogram, the application may receive the medical attestation, a digital signature of the medical attestation, and a public key of the digital signature, which may be provided in the initial data package and/or another data package generated by the contactless card responsive to another tap to the terminal. The terminal may then validate the digital signature, e.g., based on validating a certificate chain of the digital signature. The terminal may then decrypt the digital signature using the public key. The terminal may then compare the decrypted digital signature to the received medical attestation. If the comparison results in a match, e.g., the decrypted digital signature matches the medical attestation, the terminal may validate the medical attestation. The terminal may then determine that the person has proven their immunization. The terminal may then output an indication of the proven immunization and/or perform any other operation, e.g., opening a turnstile and/or door to permit entry to the public transit facilities.

Advantageously, embodiments disclosed herein provide techniques to securely prove medical attestations. By leveraging key diversification to validate the cryptogram, embodiments of the disclosure may securely verify the identity of the cardholder. By leveraging cryptography, digital signature validation, and certificate validation, embodiments disclosed herein may securely verify the medical attestation stored in the contactless card. The combination of these techniques may provide for more accurate, secure, and scalable verification of medical attestations. Furthermore, embodiments disclosed herein may preserve data privacy and/or personal privacy by limiting the exposure of sensitive information.

With general reference to notations and nomenclature used herein, one or more portions of the detailed description which follows may be presented in terms of program procedures executed on a computer or network of computers. These procedural descriptions and representations are used by those skilled in the art to most effectively convey the substances of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic, or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include digital computers as selectively activated or configured by a computer program stored within that is written in accordance with the teachings herein, and/or include apparatus specially constructed for the required purpose or a digital computer. Various embodiments also relate to apparatus or systems for performing these operations. These apparatuses may be specially constructed for the required purpose. The required structure for a variety of these machines will be apparent from the description given.

Reference is now made to the drawings, wherein like reference numerals are used to refer to like elements throughout. In the following description, for the purpose of explanation, numerous specific details are set forth in order to provide a thorough understanding thereof. It may be evident, however, that the novel embodiments can be practiced without these specific details. In other instances, well-known structures and devices are shown in block diagram form in order to facilitate a description thereof. The intention is to cover all modification, equivalents, and alternatives within the scope of the claims.

FIG. 1A depicts an exemplary system 100, consistent with disclosed embodiments. Although the system 100 shown in FIGS. 1A-1B has a limited number of elements in a certain topology, it may be appreciated that the system 100 may include more or less elements in alternate topologies as desired for a given implementation.

As shown, the system 100 comprises one or more computing devices 102, one or more contactless cards 104, and one or more authentication servers 106. The contactless card 104 is representative of any type of payment card, such as a credit card, debit card, ATM card, gift card, and the like. The contactless card 104 may comprise one or more communications interfaces 126, such as a radio frequency identification (RFID) chip, configured to communicate with a communications interface 128 of the computing devices 102 via NFC, the EMV standard, or other short-range protocols in wireless communication. Although NFC is used as an example communications protocol, the disclosure is equally applicable to other types of wireless communications, such as the EMV standard, Bluetooth, and/or Wi-Fi. The computing device 102 is representative of any number and type of computing device, such as smartphones, tablet computers, wearable devices, laptops, portable gaming devices, virtualized computing system, merchant terminals, point-of-sale systems, servers, desktop computers, and the like. The computing device 102 may be controlled by an operating system (OS) (not pictured). Example operating systems include the Android® OS, iOS®, macOS®, Linux®, and Windows® operating systems.

The server 106 is representative of any type of computing device, such as a server, workstation, compute cluster, cloud computing platform, virtualized computing system, and the like. Although not depicted for the sake of clarity, the computing device 102, contactless card 104, and server 106 each include at least one processor circuit to execute programs and/or instructions.

As shown, a memory 108 of the contactless card 104 includes an applet 110, a counter 112, a master key 114, a diversified key 116, and a unique customer identifier (ID) 118. The applet 110 is executable code configured to perform the operations described herein. The counter 112, master key 114, diversified key 116, and customer ID 118 are used to provide security in the system 100 as described in greater detail below.

A memory 120 of the computing device 102 includes a client application 122 and an attestation 124. The attestation 124 is representative of any type of health-related data, e.g., immunization records, vaccination records, health history, disease history, infection history, pathogen history, and the like. More generally, the attestation 124 may include any type of protected health information (PHI) under the Health Insurance Portability and Accountability Act (HIPAA), where such PHI was created, used, or disclosed in the course of providing a health care service, such as a diagnosis or treatment. In one example, the attestation 124 is related to the COVID-19 disease caused by the SARS-CoV-2 virus, e.g., whether a person has received a vaccination and is therefore immune to the virus, is immune based on a previous infection and the presence of antibodies in the bloodstream, and/or is not immune based on lack of vaccination and/or previous infection.

The attestation 124 may be generated by the client application 122 and/or provided to the client application 122 from a different source. The client application 122 may be any type of application that is configured to perform the techniques described herein. In at least one embodiment, the client application 122 is provided by a financial institution associated with the contactless card 104, and/or includes logic provided by the financial institution (e.g., software development kits (SDKs), APIs, etc.) configured to perform the techniques described herein. For example a medical records system may include an SDK that facilitates the cryptographic and other techniques described herein.

The attestation 124 may take any suitable format, such as words, phrases, alphanumeric codes, and the like. For example, a medical health professional may enter the relevant data for the attestation 124 via the client application 122. In such an example, a physician and/or other health professional may administer a COVID-19 vaccine to the patient. The physician may then generate the attestation 124 for the patient using the client application 122. In one embodiment, the attestation 124 includes a date of the attestation (e.g., a date the vaccine was administered), an indication of the relevant PHI (e.g., an alphanumeric code corresponding to the vaccine, a phrase indicating the person has been vaccinated, etc.), and the customer ID 118 received from the contactless card 104. As stated in greater detail below, in some embodiments, the attestation 124 may include a cryptogram (e.g., the encrypted customer ID 130) generated by the contactless card 104.

Generally, to generate and/or store the attestation 124 in the contactless card 104, the system 100 must authenticate and/or verify the identity of the user. To authenticate the identity of the user, embodiments disclosed herein may leverage the contactless card 104. More specifically, once the user requests to store the attestation 124 in the contactless card 104, the client application 122 may output a notification instructing the user to tap the contactless card 104 to the device 102. Generally, once the contactless card 104 is brought within communications range of the communications interface 128 of the device 102, the applet 110 of the contactless card 104 may generate an encrypted customer ID 130, e.g., a cryptogram, as part of the authentication process required to store the attestation 124 in the contactless card. To enable NFC data transfer between the contactless card 104 and the device 102, the client application 122 may communicate with the contactless card 104 when the contactless card 104 is sufficiently close to the communications interface 128 of the device 102.

As stated, the system 100 is configured to implement key diversification to secure data, which may be referred to as a key diversification technique herein. Generally, the server 106 (or another computing device) and the contactless card 104 may be provisioned with the same master key 114 (also referred to as a master symmetric key). More specifically, each contactless card 104 is programmed with a distinct master key 114 that has a corresponding pair in the server 106. For example, when a contactless card 104 is manufactured, a unique master key 114 may be programmed into the memory 108 of the contactless card 104. Similarly, the unique master key 114 may be stored in a record of a customer associated with the contactless card 104 in the account data 138 of the server 106 (and/or stored in a different secure location, such as the hardware security module (HSM) 140). The master key 114 may be kept secret from all parties other than the contactless card 104 and server 106, thereby enhancing security of the system 100. In some embodiments, the applet 110 of the contactless card 104 may encrypt and/or decrypt data (e.g., the customer ID 118) using the master key 114 and the data as input a cryptographic algorithm. For example, encrypting the customer ID 118 with the master key 114 may result in the encrypted customer ID 130. Similarly, the authentication server 106 may encrypt and/or decrypt data associated with the contactless card 104 using the corresponding master key 114.

In other embodiments, the master keys 114 of the contactless card 104 and server 106 may be used in conjunction with the counters 112 to enhance security using key diversification. The counters 112 comprise values that are synchronized between the contactless card 104 and server 106. The counter value 112 may comprise a number that changes each time data is exchanged between the contactless card 104 and the server 106 (and/or the contactless card 104 and the device 102). When preparing to send data (e.g., to the server 106 and/or the device 102), the contactless card 104 may increment the counter value 112. The contactless card 104 may then provide the master key 114 and counter value 112 as input to a cryptographic algorithm, which produces a diversified key 116 as output. The cryptographic algorithm may include encryption algorithms, hash-based message authentication code (HMAC) algorithms, cipher-based message authentication code (CMAC) algorithms, and the like. Non-limiting examples of the cryptographic algorithm may include a symmetric encryption algorithm such as 3DES or AES128; a symmetric HMAC algorithm, such as IIMAC-SIIA-256; and a symmetric CMAC algorithm such as AES-CMAC. Examples of key diversification techniques are described in greater detail in U.S. patent application Ser. No. 16/205,119, filed Nov. 29, 2018. The aforementioned patent application is incorporated by reference herein in its entirety.

Continuing with the key diversification example, the contactless card 104 may then encrypt the data (e.g., the customer ID 118 and/or any other data) using the diversified key 116 and the data as input to the cryptographic algorithm. For example, encrypting the customer ID 118 with the diversified key 116 may result in the encrypted customer ID 130.

Regardless of the encryption technique used, the contactless card 104 may then transmit the encrypted data (e.g., the encrypted customer ID 130) to the client application 122 of the device 102 (e.g., via an NFC connection, Bluetooth connection, etc.). The client application 122 of the device 102 may then transmit the encrypted customer ID 130 to the server 106 via the network 132. In at least one embodiment, the contactless card 104 transmits the counter value 112 with the encrypted data. In such embodiments, the contactless card 104 may transmit an encrypted counter value 112, or an unencrypted counter value 112.

Once received, the authentication application 134 may authenticate the encrypted customer ID 130. For example, the authentication application 134 may attempt to decrypt the encrypted customer ID 130 using a copy of the master key 114 stored in the memory 136 of the authentication server 106. In another example, the authentication application 134 may provide the master key 114 and counter value 112 as input to the cryptographic algorithm, which produces a diversified key 116 as output. The resulting diversified key 116 may correspond to the diversified key 116 of the contactless card 104, which may be used to decrypt the encrypted customer ID 130.

Regardless of the decryption technique used, the authentication application 134 may successfully decrypt the encrypted customer ID 130, thereby verifying the encrypted customer ID 130 (e.g., by comparing the resulting customer ID 118 to a customer ID stored in the account data 138, and/or based on an indication that the decryption using the key 114 and/or 116 was successful). Although the keys 114, 116 are depicted as being stored in the memory 136, the keys 114, 116 may be stored elsewhere, such as in a secure element and/or the HSM 140. In such embodiments, the secure element and/or the HSM 140 may decrypt the encrypted customer ID 130 using the keys 114 and/or 116 and a cryptographic function. Similarly, the secure element and/or HSM 140 may generate the diversified key 116 based on the master key 114 and counter value 112 as described above.

If, however, the authentication application 134 is unable to decrypt the encrypted customer ID 130 to yield the expected result (e.g., the customer ID 118 of the account associated with the contactless card 104), the authentication application 134 does not validate the encrypted customer ID 130. In such an example, the authentication application 134 transmits an indication of the failed verification to the client application 122. As such, the client application 122 may reject performance of the requested storing of the attestation 124 to preserve the security of the attestation 124.

Figure 1B:
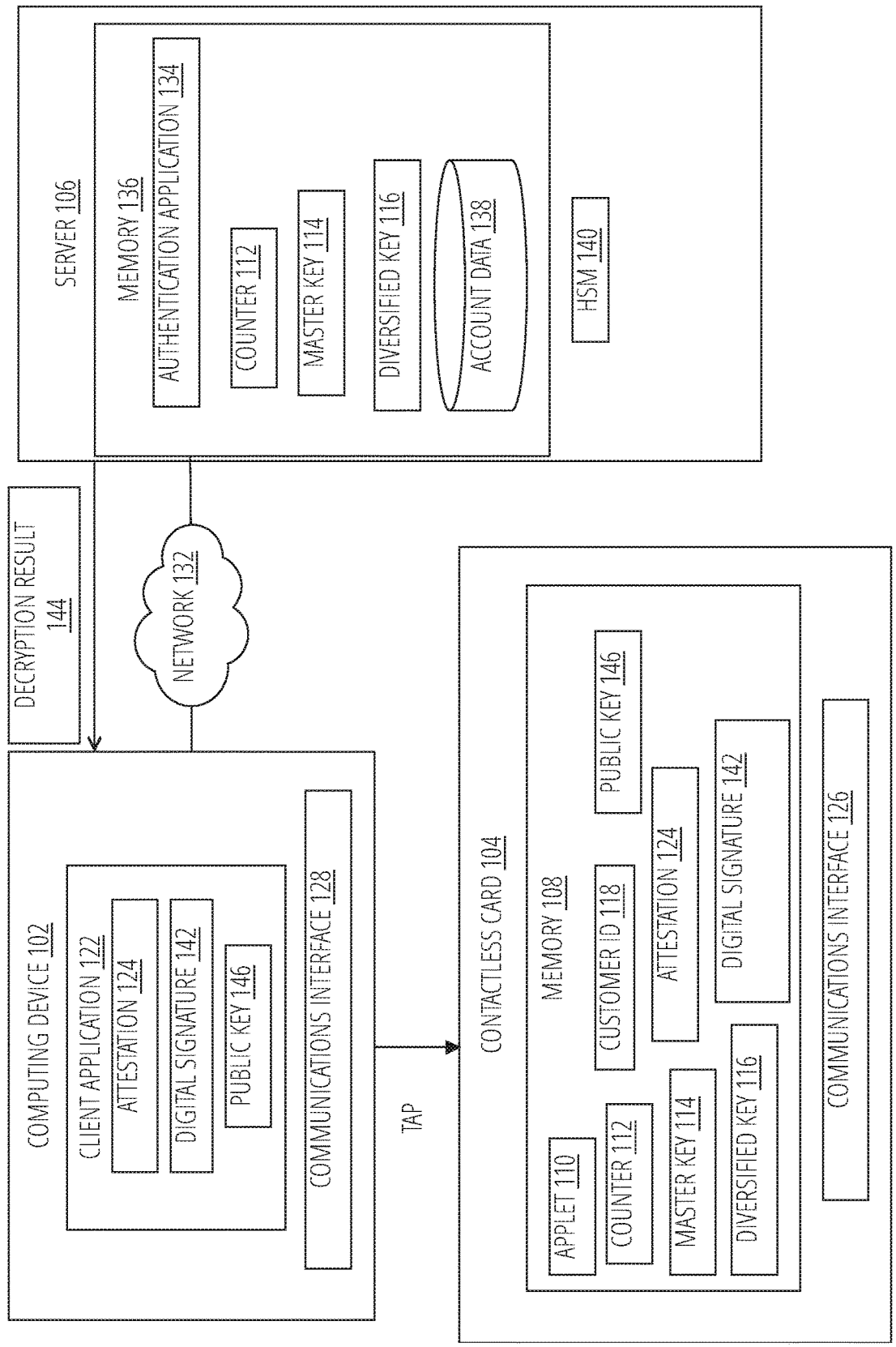

FIG. 1B illustrates an embodiment where the authentication application 134 has successfully decrypted the encrypted customer ID 130, thereby verifying (or authenticating) the cryptogram, and by association, the identity of the user. As shown, the authentication application 134 transmits a decryption result 144 to the device 102, where the decryption result 144 indicates that the authentication application 134 successfully decrypted the encrypted customer ID 130. Responsive to receiving the decryption result 144, the client application 122 may determine that the authentication application 134 successfully decrypted the encrypted customer ID 130. Based on this determination, the client application 122 may determine to proceed with the process of storing the medical attestation 124 in the card 104.

To improve security and privacy, the client application 122 may compute a digital signature 142 of the attestation 124 using a private key (not pictured). Generally, the attestation 124 and the private key may be provided as input to an algorithm that computes the digital signature 142. The public key 146 may correspond to the private key and may be used to decrypt the digital signature 142.

Therefore, continuing with the previous example, the attestation 124 may include a date the vaccine was administered to the patient, an indication of the relevant PHI (e.g., an alphanumeric code corresponding to the vaccine, a phrase indicating the person has been vaccinated, etc.), the customer ID 118 received from the contactless card 104. Therefore, the digital signature 142 may include a signature of the date, the PHI, the customer ID 118. As stated, in some embodiments, the attestation 124 includes the encrypted customer ID 130. In such embodiments, the digital signature 142 further includes a signature of the encrypted customer ID 130.

As shown, the client application 122 may then instruct the user to tap the contactless card 104 to the device 102. Doing so causes the client application 122 to transfer the attestation 124, digital signature 142, and the public key 146 to the contactless card 104. The applet 110 may then store the attestation 124, digital signature 142, and the public key 146 in the memory 108.

Figure 2A:
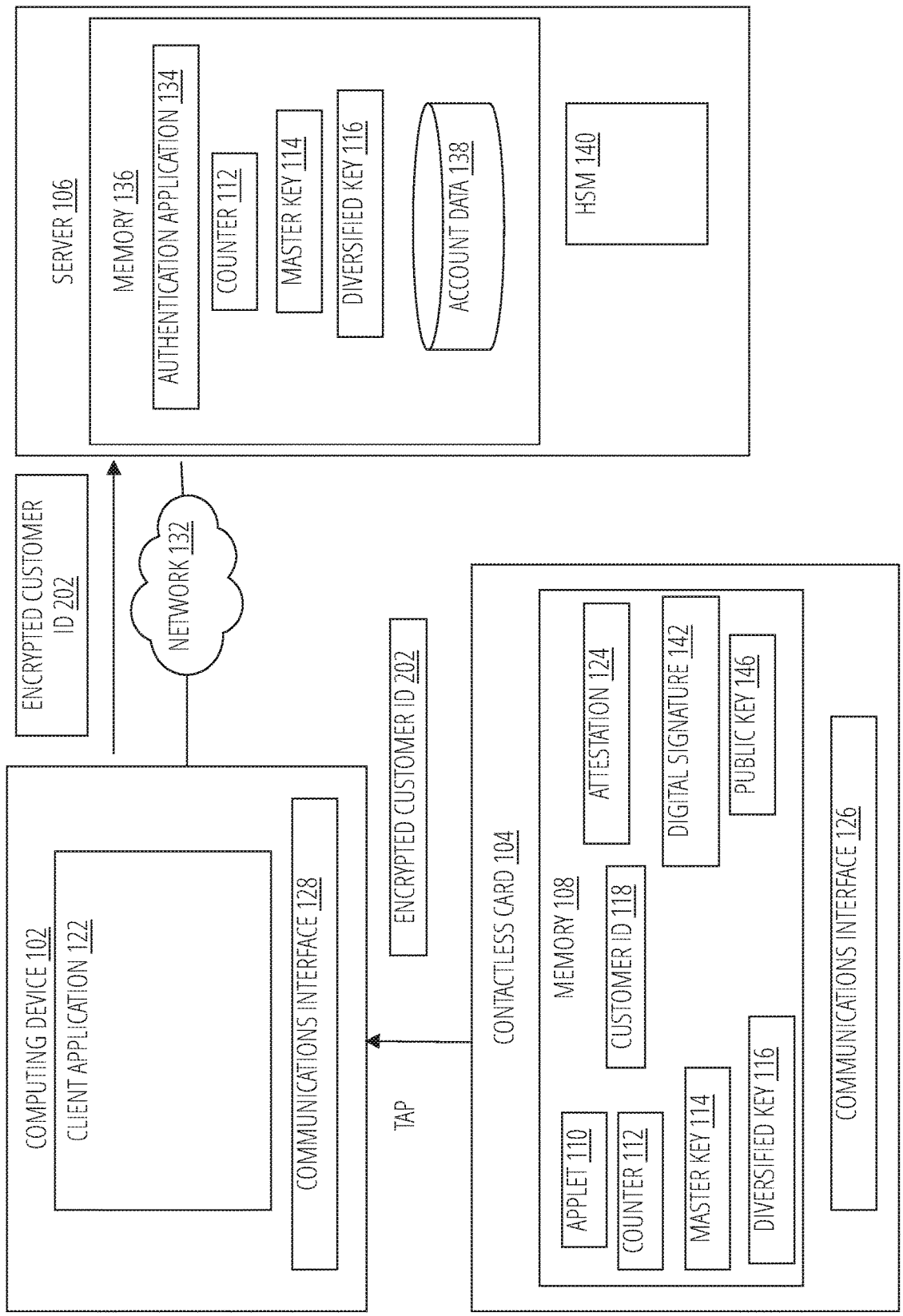
FIGS. 2A-2C illustrate embodiments of a system.

FIG. 2A depicts a schematic of an exemplary system 200, consistent with disclosed embodiments. Although the system 200 shown in FIGS. 2A-2C has a limited number of elements in a certain topology, it may be appreciated that the system 200 may include more or less elements in alternate topologies as desired for a given implementation.

As shown, the system 200 includes the computing device 102, contactless card 104, and server 106. Generally, FIG. 2A depicts an embodiment where the medical attestation 124 stored in the contactless card 104 is used to verify a medical status of a user. For example, the user may require proof of immunity to the COVID-19 disease, e.g., via vaccination or otherwise. In such examples, the user of the computing device 102 may request to use the attestation 124 to prove the immunity to COVID-19. In some embodiments, the user may provide authentication credentials to client application 122 to access the account associated with the contactless card 104 (e.g., an account reflected in the account data 138). For example, the authentication credentials may include a username (or login) and password, biometric credentials (e.g., fingerprints, Face ID, etc.), and the like.

The client application 122 may then instruct the user to tap the contactless card 104 to the computing device 102. Doing so causes the applet 110 of the contactless card 104 to generate an encrypted customer ID 202 based on the customer ID 118 and the diversified key 116 generated as described above. The applet 110 may then transmit the encrypted customer ID 202 to the device 102, e.g., via NFC. Once received, the client application 122 may transmit the encrypted customer ID 202 to the authentication application 134.

Once received, the authentication application 134 may authenticate the encrypted customer ID 202. For example, the authentication application 134 may attempt to decrypt the encrypted customer ID 202 by providing the master key 114 and incremented counter value 112 as input to the cryptographic algorithm, which produces the diversified key 116 as output. The resulting diversified key 116 may correspond to the instance of the diversified key 116 generated by the contactless card 104 to create the encrypted ID 202, which may be used to decrypt the encrypted customer ID 202. Generally, the authentication application 134 may transmit a decryption result to the client application 122 indicating whether the decryption was successful or unsuccessful.

Figure 2B:
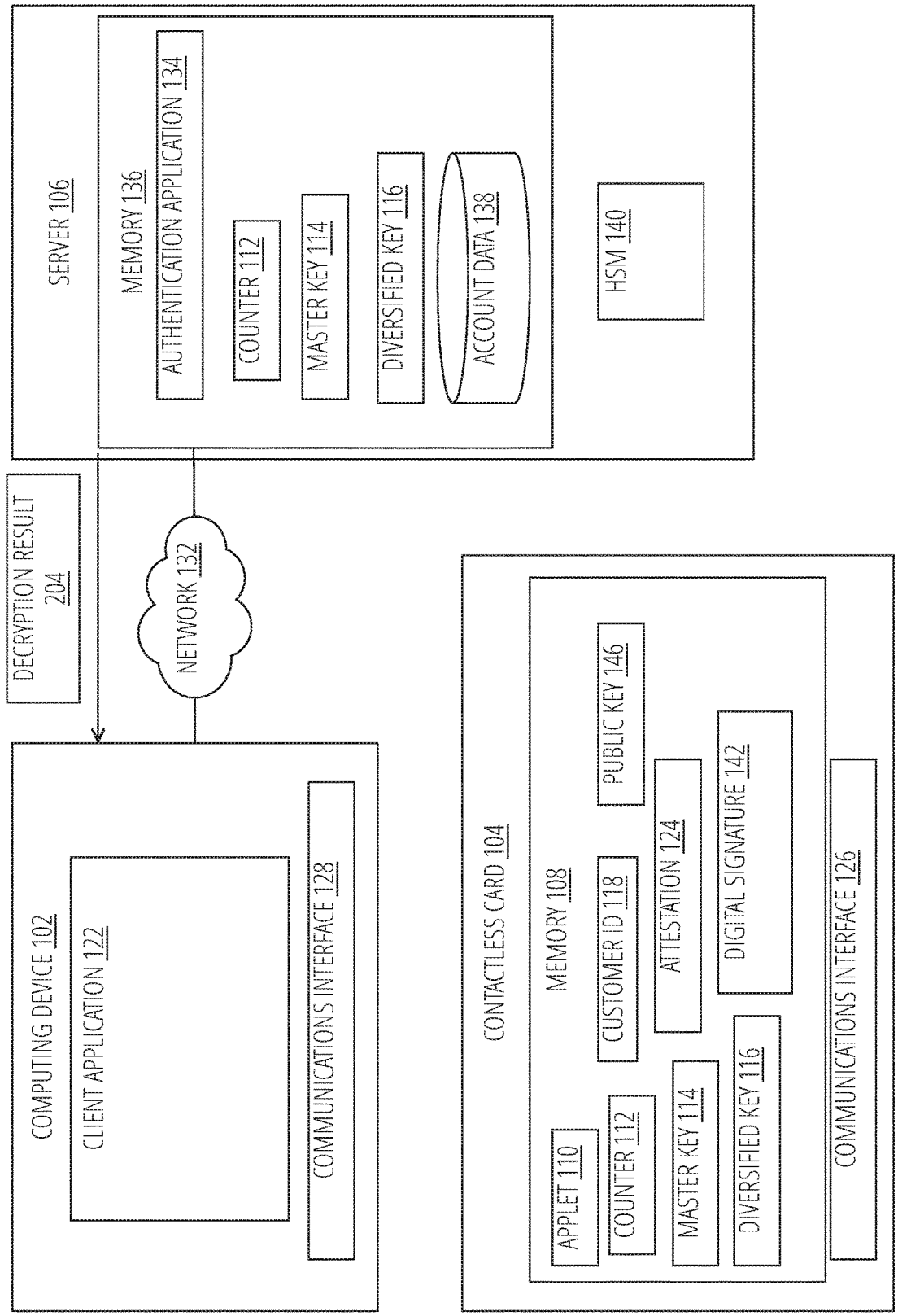

FIG. 2B illustrates an embodiment where the authentication application 134 successfully decrypted the encrypted customer ID 202. In response, the authentication application 134 transmits a decryption result 204 to the computing device 102 indicating that the encrypted customer ID 202 was decrypted. Based on the decryption result 204, the client application 122 determines that the encrypted customer ID 202 was decrypted. If the client application 122 determines that the decryption was not successful, the client application 122 may restrict any further operations to prevent unauthorized exposure of the attestation 124.

Figure 2C:
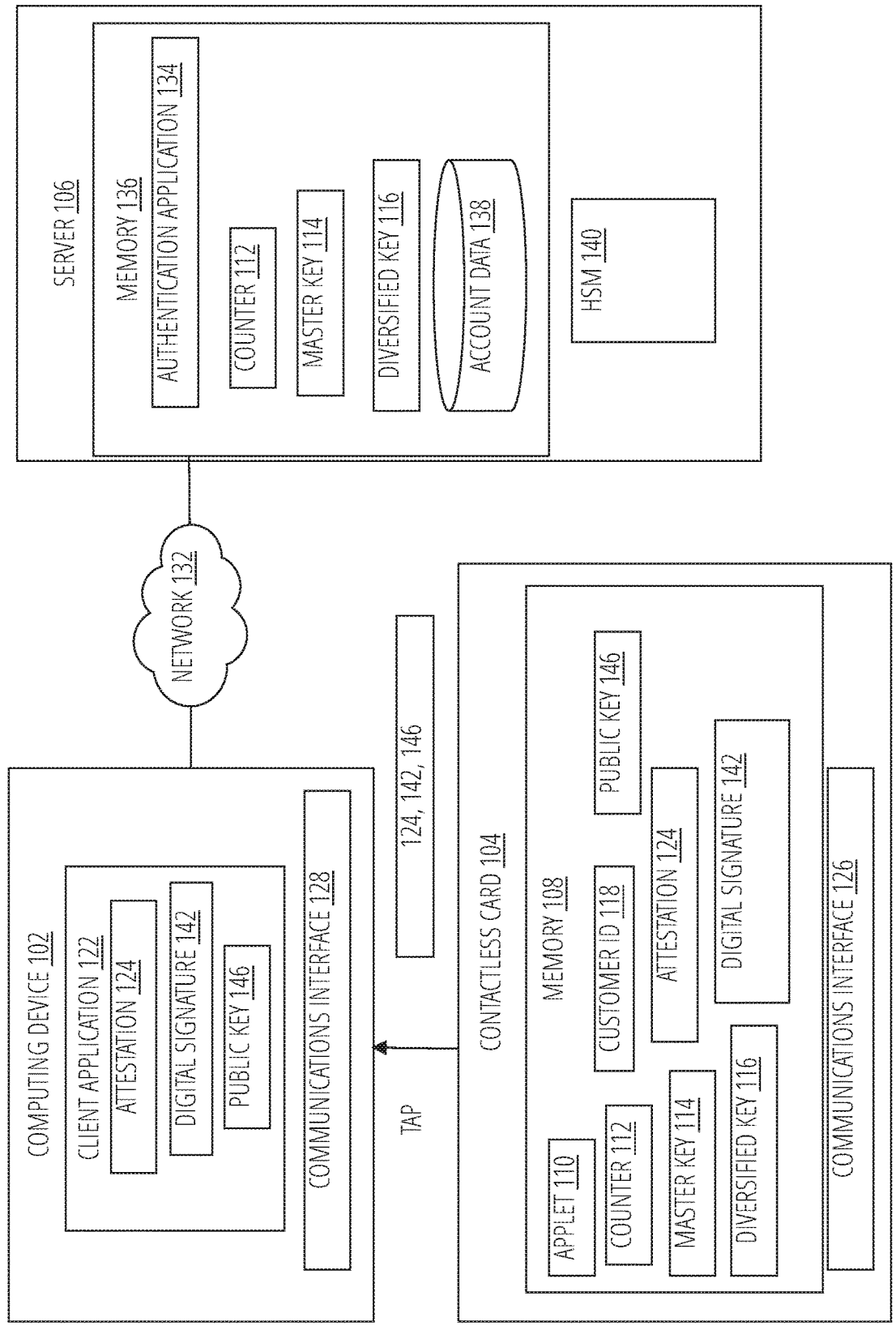

FIG. 2C illustrates an embodiment where the client application 122 instructs the user to tap the contactless card 104 to the device 102. Doing so causes the applet 110 to transmit the attestation 124, digital signature 142 of the attestation 124, and public key 146 of the digital signature 142 to the device 102. Although depicted as being transmitted based on separate taps of the card to the device, in some embodiments, the encrypted customer ID 202, the attestation 124, the digital signature 142, and public key 146 may be transmitted to the client application 122 via a single tap of the card to the device. In such embodiments, the client application 122 parses these elements to perform the functionality described herein.

In some embodiments, the applet 110 may provide a zero-knowledge proof of the medical attestation 124, e.g., without exposing any information that may personally identify the user and/or the underlying PHI of the medical attestation 124. More generally, the applet 110 and/or the client application 122 may include a protocol of conformity that includes one or more rules for processing the attestation 124, digital signature 142, and/or public key 146. For example, the rules of the applet 110 and/or client application 122 may require validation of a certificate chain for the digital signature 142 and/or the public key 146. Generally, when the attestation 124 is stored in the card, the public key 146 and/or digital signature 142 may be associated with a certificate of the entity signing the attestation 124 (e.g., the medical entity, the issuer of the contactless card 104, a governmental agency, etc.). The certificate may include one or more cryptographic elements (e.g., a digital signature) that may be decrypted or verified by the applet 110 and/or the client application 122 using a corresponding public key.

If multiple entities sign the attestation 124, each entity may have an associated certificate. In such embodiments, these certificates link to form a certificate chain, and the digital signature of each certificate in the chain may be verified (e.g., decrypted using the corresponding public key) by the applet 110 and/or the client application 122. If each certificate is not verified, the applet 110 and/or the client application 122 may refrain from exposing the medical attestation 124. In some embodiments, the certificates may be stored by the contactless card and/or the client application 122. In other embodiments, the client application 122 may receive the certificates from a certificate authority (not pictured) via the network 132.

In another example, one or more rules of the applet 110 and/or the client application 122 may require that at least one known (or predefined) entity sign the attestation 124. For example, the rules may require one or more of a governmental agency, the financial institution associated with the contactless card 104, a hospital, laboratory, or other entity to have signed the attestation. If the certificate chain does not indicate that the at least one known entity has signed the attestation and/or the associated certificate is not validated, the applet 110 and/or the client application 122 may refrain from exposing the medical attestation 124.

As shown in FIG. 2C, all rules have been satisfied and the client application 122 receives the attestation 124, digital signature 142, and public key 146 from the contactless card 104. As stated, in some embodiments, the attestation 124 includes a cryptogram (e.g., the encrypted customer ID 130). In such embodiments, the rules of the client application 122 may require validation of this cryptogram prior to exposing the medical attestation 124. In such embodiments, the client application 122 may extract the encrypted customer ID 130 and transmit the encrypted customer ID 130 to the server 106 for verification. Because the diversified key used to generate the encrypted customer ID 130 would not be reproduced using the most current counter value 112, the server 106 may store the diversified key 116 used to decrypt the initial instance of the encrypted customer ID 130. Additionally and/or alternatively, the attestation 124 may include the counter value 112 used to generate the diversified key 116 that produced the encrypted customer ID 130, and the client application 122 may send this counter value 112 to the server 106 with the encrypted customer ID 130. Doing so allows the server 106 to subsequently decrypt the encrypted customer ID 130 included in the medical attestation 124 using the diversified key 116. The server 106 may then transmit a decryption result to the client application 122. If the decryption of the encrypted customer ID 130 is not successful, the client application 122 may refrain from exposing the medical attestation 124. If the decryption of the encrypted customer ID 130 is successful, the client application 122 may continue processing.

If all rules have been satisfied, including the optional decryption of the encrypted customer ID 130 in the attestation 124, the client application 122 may decrypt the digital signature 142. The client application 122 may then compare the digital signature 142 to the attestation 124. If the comparison results in a match, the client application 122 may verify the medical attestation 124. Because the digital signature 142 combines each data element cryptographically, the attestation 124 must be unmodified to match the decrypted digital signature 142. If the attestation 124 is tampered or modified in any way, the comparison to the decrypted digital signature 142 may fail. If the attestation 124 is not modified, the comparison to the decrypted digital signature 142 may pass, and the client application 122 verifies the attestation 124.

If the client application 122 verifies the attestation based on the comparison resulting in a match, the client application 122 may generate an attestation result. The attestation result may generally reflect the medical attestation 124, e.g., that the user is immune and/or not immune to COVID-19, or any other medical condition. In some embodiments, the client application 122 outputs the attestation result and/or the attestation 124 on a display of the device 102. In addition and/or alternatively, the client application 122 may transmit the attestation 124 and/or attestation result to another computing device 102, e.g., via email, text message, push notification, etc. In some embodiments, the device 102 is a mobile device that may communicate with other card reading devices using NFC. In such examples, the client application 122 may generate an NDEF file that includes the attestation 124 and/or the attestation result that can be read by another device 102 via NFC.

For example, if a public transit system includes computing devices 102 comprising a plurality of terminals, point of sale devices, or other computing devices 102, the user may need to prove immunity from COVID-19 to use the public transit. In such embodiments, the user may tap the contactless card 104 directly to the terminal. The terminal may then perform the operations described herein to verify the encrypted customer IDs 202 and/or 130 and verify the attestation 124 stored in the contactless card 104 (including certificate validation, decryption of digital signature 142, and comparison). In other examples, the terminal may communicate with the computing device 102 of the user (e.g., a smartphone) to request the medical attestation 124. In such embodiments, the device of the user 102 operates as described above and transmits the attestation result to the terminal.

When receiving the attestation result, the terminal 102 may perform one or more operations in response. For example, if the attestation result indicates the person was recently diagnosed with COVID-19 (e.g., within a predefined number of days), the terminal 102 may restrict access to public transit systems, public places, private places, etc., by locking doors, locking turnstiles, initiating an alarm, etc. Similarly, if the attestation result indicates the person is immune to COVID-19 and/or is otherwise healthy, the terminal 102 may permit access to the public transit or other places by unlocking doors, turnstiles, etc. Similarly, the client application 122 may perform and/or initiate these and/or other operations in response to a determination to expose the medical attestation 124.

In some embodiments, the client application 122 may decode the decrypted digital signature 142 and/or the attestation 124. As stated, in some embodiments, different coding schemes may be used to encode a medical attestation 124. Therefore, in such embodiments, the client application 122 ensures that the proper comparison is being made (e.g., comparing encoded data to encoded data and/or comparing decoded data to decoded data). Similarly, the client application 122 may decode and/or encode the medical attestation 124 to provide output that is readable by a user (e.g., converting an alphanumeric string to a word or phrase that conveys a specific medical status, such as immunity to COVID-19).

Figure 3A:
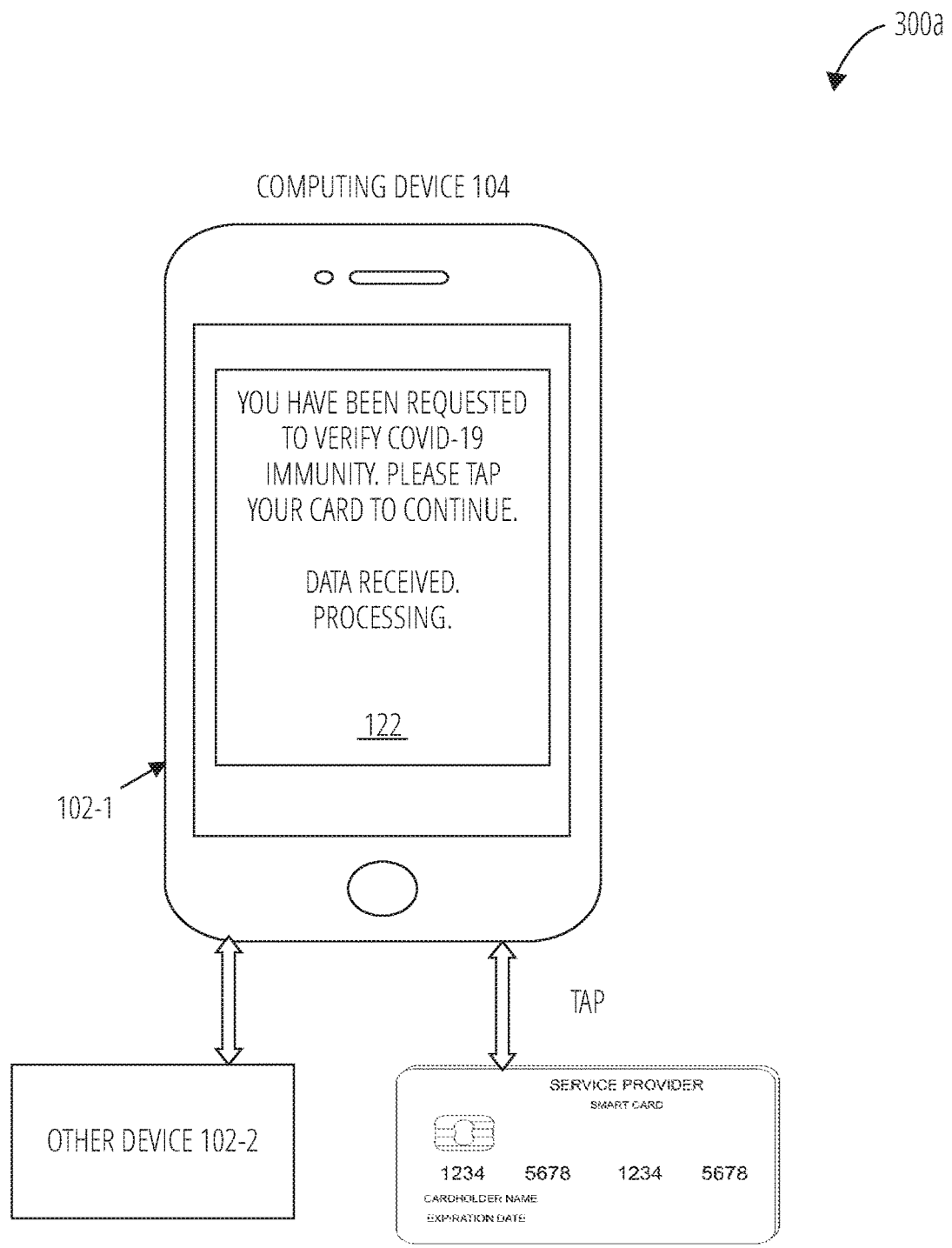
FIGS. 3A-3B illustrate embodiments of a system.

FIG. 3A is a schematic 300a illustrating an example mobile computing device 102-1. As shown, the client application 122 outputs a notification specifying to tap a contactless card 104 to the device 102 to prove that the user is immune to COVID-19. In one embodiment, the application 122 receives a request from the other device 102-2 to prove immunity. In another embodiment, the application 122 outputs the notification without receiving a request from an external device.

As shown, the user may tap the contactless card 104 to the computing device 102-1. Doing so causes the applet 110 of the contactless card 104 to generate a cryptogram (e.g., an encrypted customer ID) based on the customer ID 118 and a diversified key 116 as described above. The applet 110 may then transmit the cryptogram to the device 102-1, e.g., via NFC. As stated, in some embodiments, the contactless card 104 transmits the attestation 124, digital signature 142, and public key 146 to the device 102-1 with the cryptogram. Once received, the client application 122 may transmit the cryptogram to the authentication application 134 for processing.

Once received, the authentication application 134 may attempt to verify the cryptogram. For example, the authentication application 134 may attempt to decrypt the cryptogram by providing the master key 114 and incremented counter value 112 as input to the cryptographic algorithm, which produces the diversified key 116 as output. The resulting diversified key 116 may correspond to the instance of the diversified key 116 generated by the contactless card 104 to create the cryptogram, which may be used to decrypt the cryptogram. Generally, the authentication application 134 may transmit a decryption result to the client application 122 indicating whether the decryption was successful or unsuccessful.

Figure 3B:
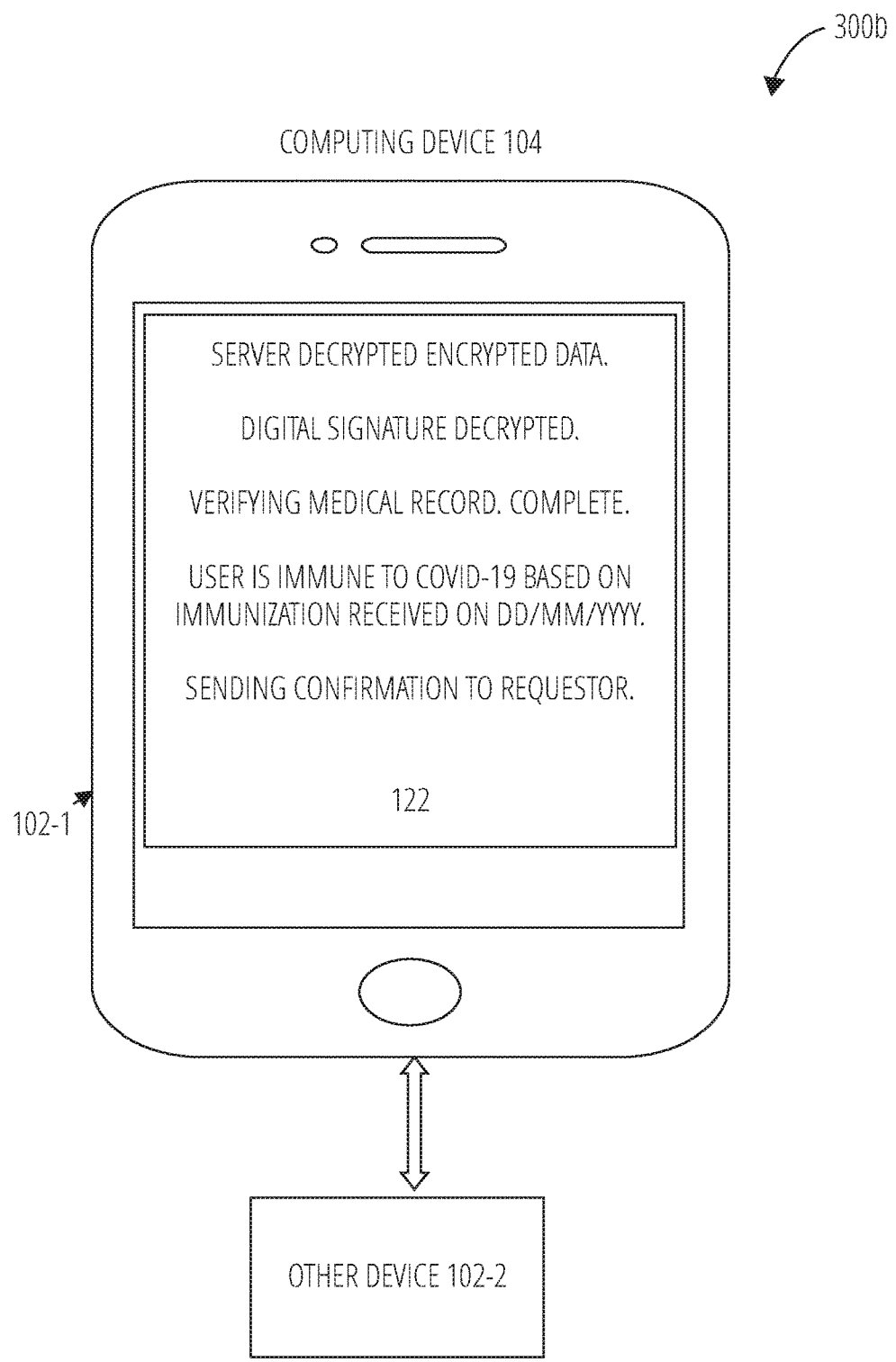

FIG. 3B is a schematic 300b illustrating an example where the client application 122 receives a decryption result indicating the authentication server decrypted the cryptogram. In response, the client application 122 attempts to decrypt the digital signature 142. If the client application 122 has not received the attestation 124, digital signature 142, and/or public key 146, the client application 122 may instruct the user to tap the card to the device 102, which causes the applet 110 to transmit the attestation 124, digital signature 142, and/or public key 146 based on the decryption of the cryptogram by the server.

The client application 122 may then verify the certificate chain of the digital signature 142 and decrypt the digital signature 142. The client application 122 may then compare the decrypted digital signature 142 to the attestation 124. If a match exists, the client application 122 verifies the medical records included in the attestation 124. The client application 122 may then output an indication specifying an attestation result, e.g., that the user is immune to COVID-19. As stated, the client application 122 may transmit an indication of the attestation result to the requesting device 102-2, e.g., via Wi-Fi and/or NFC.

Furthermore, the client application 122 and/or requesting device 102-2 may perform and/or initiate performance of any number and/or types of operations based on the attestation result. For example, if the request indicates to determine whether a person has COVID-19, the client application 122 and/or the requesting device 102-2 may close access points to public places, public transit, buildings, etc., based a determination that the verified medical attestation 124 indicates the person was diagnosed with COVID-19 within a predefined number of days. Similarly, if the verified medical attestation 124 indicates the person is immune to COVID-19 via vaccine, the client application 122 and/or the requesting device 102-2 may open access points to public places, public transit, buildings, etc.

Figure 4A:
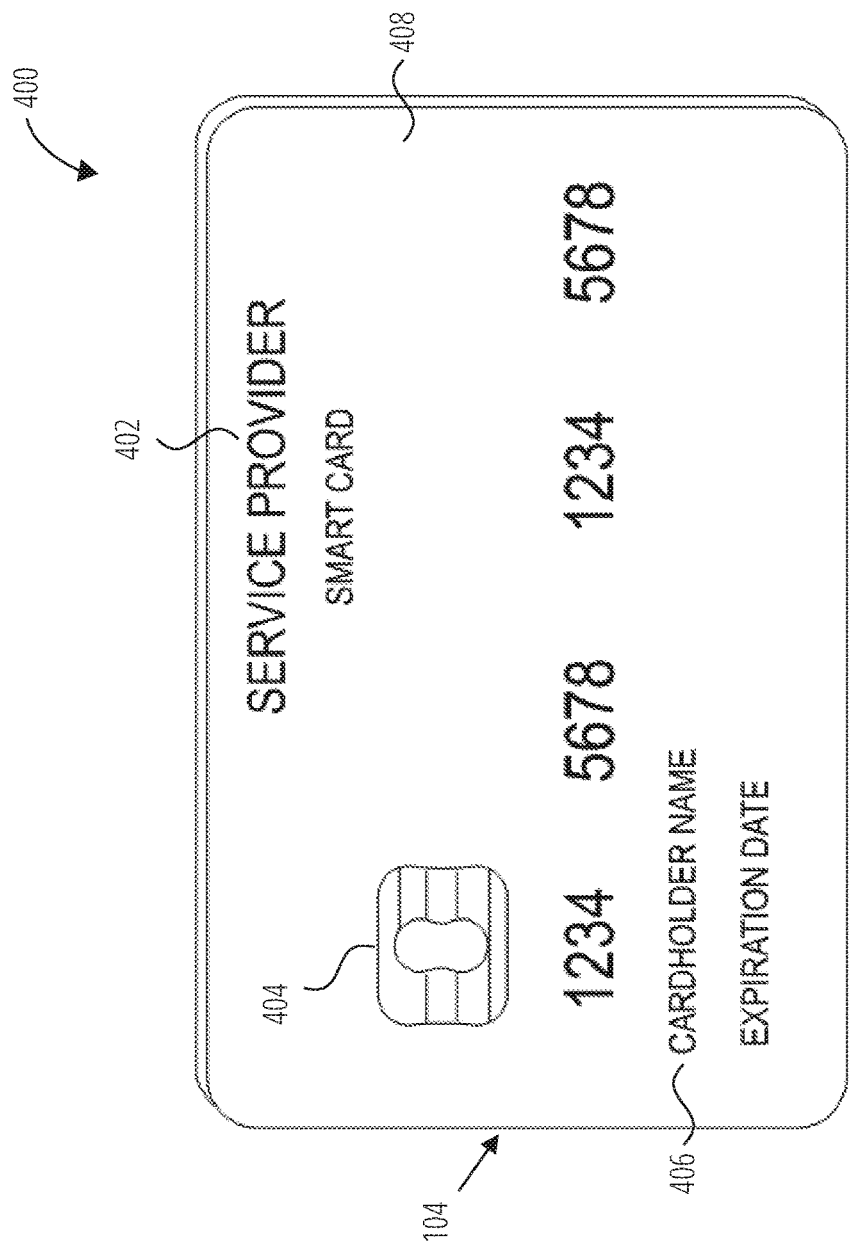
FIGS. 4A-4B illustrate an example contactless card.

FIG. 4A is a schematic 400 illustrating an example configuration of a contactless card 104, which may include a payment card, such as a credit card, debit card, or gift card, issued by a service provider as displayed as service provider indicia 402 on the front or back of the contactless card 104. In some examples, the contactless card 104 is not related to a payment card, and may include, without limitation, an identification card. In some examples, the contactless card may include a dual interface contactless payment card, a rewards card, and so forth. The contactless card 104 may include a substrate 408, which may include a single layer or one or more laminated layers composed of plastics, metals, and other materials. Exemplary substrate materials include polyvinyl chloride, polyvinyl chloride acetate, acrylonitrile butadiene styrene, polycarbonate, polyesters, anodized titanium, palladium, gold, carbon, paper, and biodegradable materials. In some examples, the contactless card 104 may have physical characteristics compliant with the ID-1 format of the ISO/IEC 7810 standard, and the contactless card may otherwise be compliant with the ISO/IEC 14443 standard. However, it is understood that the contactless card 104 according to the present disclosure may have different characteristics, and the present disclosure does not require a contactless card to be implemented in a payment card.

Figure 4B:
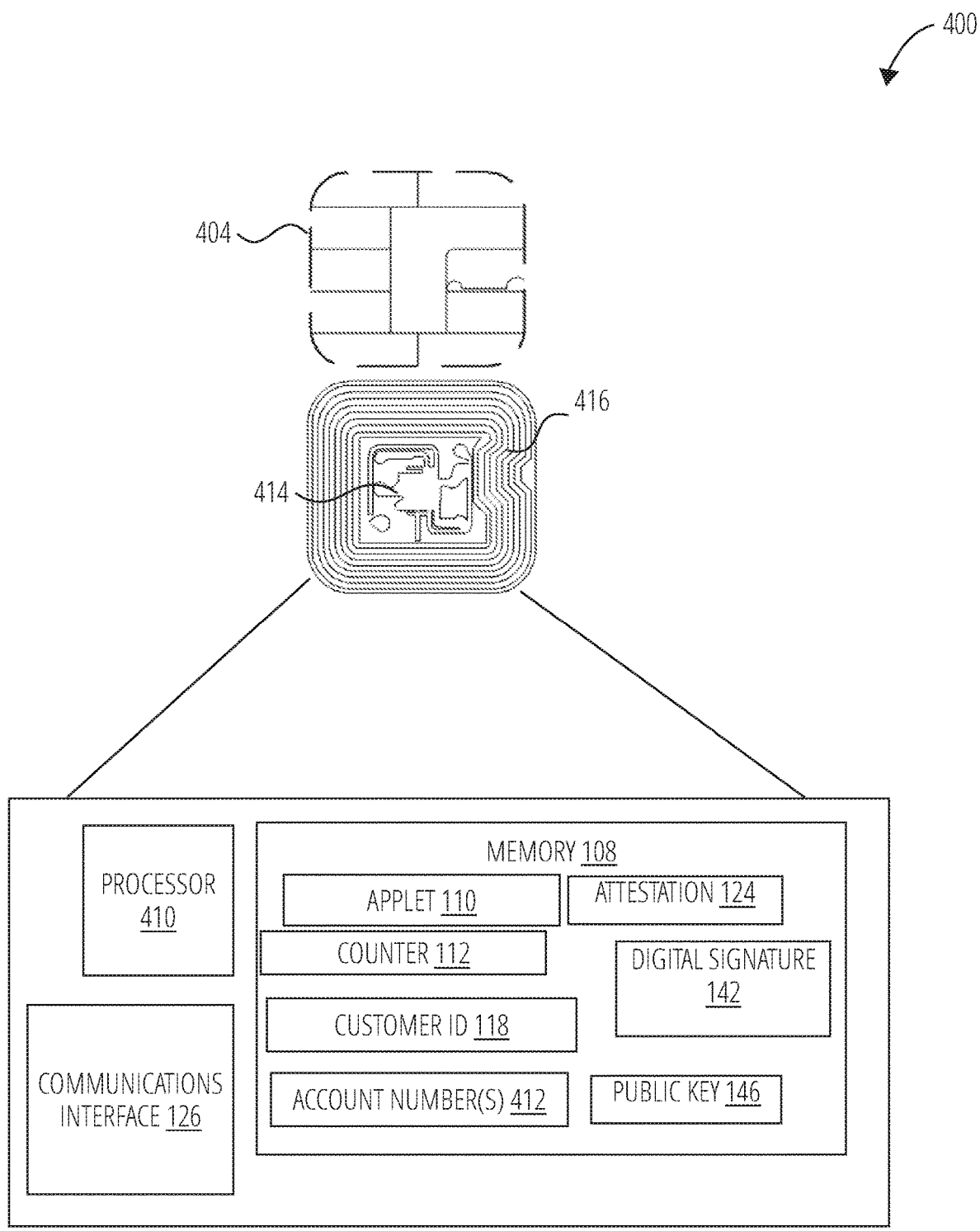

The contactless card 104 may also include identification information 406 displayed on the front and/or back of the card, and a contact pad 404. The contact pad 404 may include one or more pads and be configured to establish contact with another client device, such as an ATM, a user device, smartphone, laptop, desktop, or tablet computer via contactless cards. The contact pad may be designed in accordance with one or more standards, such as ISO/IEC 7816 standard, and enable communication in accordance with the EMV protocol. The contactless card 104 may also include processing circuitry, antenna and other components as will be further discussed in FIG. 4B. These components may be located behind the contact pad 404 or elsewhere on the substrate 408, e.g. within a different layer of the substrate 408, and may electrically and physically coupled with the contact pad 404. The contactless card 104 may also include a magnetic strip or tape, which may be located on the back of the card (not shown in FIG. 4A). The contactless card 104 may also include a Near-Field Communication (NFC) device coupled with an antenna capable of communicating via the NFC protocol. Embodiments are not limited in this manner.

As illustrated, the contact pad 404 of contactless card 104 may include processing circuitry 414 for storing, processing, and communicating information, including a processor 410, a memory 108, and one or more communications interface 126. It is understood that the processing circuitry 414 may contain additional components, including processors, memories, error and parity/CRC checkers, data encoders, anti-collision algorithms, controllers, command decoders, security primitives and tamper proofing hardware, as necessary to perform the functions described herein.

The memory 108 may be a read-only memory, write-once read-multiple memory or read/write memory, e.g., RAM, ROM, and EEPROM, and the contactless card 104 may include one or more of these memories. A read-only memory may be factory programmable as read-only or one-time programmable. One-time programmability provides the opportunity to write once then read many times. A write once/read-multiple memory may be programmed at a point in time after the memory chip has left the factory. Once the memory is programmed, it may not be rewritten, but it may be read many times. A read/write memory may be programmed and re-programed many times after leaving the factory. A read/write memory may also be read many times after leaving the factory. In some instances, the memory 108 may be encrypted memory utilizing an encryption algorithm executed by the processor 410 to encrypt data.

The memory 108 may be configured to store one or more applets 110, one or more counters 112, a customer ID 118, and one or more account number(s) 412, which may be virtual account numbers. The one or more applets 110 may comprise one or more software applications configured to execute on one or more contactless cards, such as a Java® Card applet. However, it is understood that applets 110 are not limited to Java Card applets, and instead may be any software application operable on contactless cards or other devices having limited memory. The one or more counters 112 may comprise a numeric counter sufficient to store an integer. The customer ID 118 may comprise a unique alphanumeric identifier assigned to a user of the contactless card 104, and the identifier may distinguish the user of the contactless card from other contactless card users. In some examples, the customer ID 118 may identify both a customer and an account assigned to that customer and may further identify the contactless card 104 associated with the customer's account. As stated, the account number(s) 412 may include thousands of one-time use virtual account numbers associated with the contactless card 104.

The processor 410 and memory elements of the foregoing exemplary embodiments are described with reference to the contact pad 404, but the present disclosure is not limited thereto. It is understood that these elements may be implemented outside of the contact pad 404 or entirely separate from it, or as further elements in addition to processor 410 and memory 108 elements located within the contact pad 404.

In some examples, the contactless card 104 may comprise one or more antenna(s) 416. The one or more antenna(s) 416 may be placed within the contactless card 104 and around the processing circuitry 414 of the contact pad 404. For example, the one or more antenna(s) 416 may be integral with the processing circuitry 414 and the one or more antenna(s) 416 may be used with an external booster coil. As another example, the one or more antenna(s) 416 may be external to the contact pad 404 and the processing circuitry 414.

In an embodiment, the coil of contactless card 104 may act as the secondary of an air core transformer. The terminal may communicate with the contactless card 104 by cutting power or amplitude modulation. The contactless card 104 may infer the data transmitted from the terminal using the gaps in the power connection of the contactless card 104, which may be functionally maintained through one or more capacitors. The contactless card 104 may communicate back by switching a load on the coil or load modulation. Load modulation may be detected in the terminal's coil through interference. More generally, using the antenna(s) 416, processor 410, and/or the memory 108, the contactless card 104 provides a communications interface to communicate via NFC, Bluetooth, and/or Wi-Fi communications.

As explained above, contactless card 104 may be built on a software platform operable on smart cards or other devices having limited memory, such as JavaCard, and one or more or more applications or applets may be securely executed. Applet 110 may be added to contactless cards to provide a one-time password (OTP) for multifactor authentication (MFA) in various mobile application-based use cases. Applet 110 may be configured to respond to one or more requests, such as near field data exchange requests, from a reader, such as a mobile NFC reader (e.g., of a mobile device or point-of-sale terminal) and produce an NDEF message that comprises a cryptographically secure OTP encoded as an NDEF text tag.

One example of an NDEF OTP is an NDEF short-record layout (SR=1). In such an example, one or more applets 110 may be configured to encode the OTP as an NDEF type 4 well known type text tag. In some examples, NDEF messages may comprise one or more records. The applets 110 may be configured to add one or more static tag records in addition to the OTP record.

In some examples, the one or more applets 110 may be configured to emulate an RFID tag. The RFID tag may include one or more polymorphic tags. In some examples, each time the tag is read, different cryptographic data is presented that may indicate the authenticity of the contactless card 104. Based on the one or more applet 110, an NFC read of the tag may be processed, the data may be transmitted to a server, such as a server of a banking system, and the data may be validated at the server.

In some examples, the contactless card 104 and server 106 may include certain data such that the card may be properly identified. The contactless card 104 may include one or more unique identifiers (not pictured). Each time a read operation takes place, the counter 112 may be configured to increment. In some examples, each time data from the contactless card 104 is read (e.g., by a computing device 102), the counter 112 is transmitted to the server for validation and determines whether the counter 112 are equal (as part of the validation) to a counter of the server.

The one or more counter 112 may be configured to prevent a replay attack. For example, if a cryptogram has been obtained and replayed, that cryptogram is immediately rejected if the counter 112 has been read or used or otherwise passed over. If the counter 112 has not been used, it may be replayed. In some examples, the counter that is incremented on the card is different from the counter that is incremented for transactions. The contactless card 104 is unable to determine the application transaction counter 112 since there is no communication between applet 110 on the contactless card 104. In some examples, the contactless card 104 may comprise a first applet 110-1, which may be a transaction applet, and a second applet 110-2, which may be a medical attestation applet for processing one or more medical attestations 124 stored in the contactless card 104. Each applet 110-1 and 110-2 may comprise a respective counter 112.

In some examples, the counter 112 may get out of sync. In some examples, to account for accidental reads that initiate transactions, such as reading at an angle, the counter 112 may increment but the application does not process the counter 112. In some examples, when the device 102 is woken up, NFC may be enabled and the device 102 may be configured to read available tags, but no action is taken responsive to the reads.

To keep the counter 112 in sync, an application, such as a background application, may be executed that would be configured to detect when the device 102 wakes up and synchronize with the server of a banking system indicating that a read that occurred due to detection to then move the counter 112 forward. In other examples, Hashed One Time Password may be utilized such that a window of mis-synchronization may be accepted. For example, if within a threshold of 10, the counter 112 may be configured to move forward. But if within a different threshold number, for example within 10 or 1000, a request for performing re-synchronization may be processed which requests via one or more applications that the user tap, gesture, or otherwise indicate one or more times via the user's device. If the counter 112 increases in the appropriate sequence, then it possible to know that the user has done so.

The key diversification technique described herein with reference to the counter 112, master key, and diversified key, is one example of encryption and/or decryption a key diversification technique. This example key diversification technique should not be considered limiting of the disclosure, as the disclosure is equally applicable to other types of key diversification techniques.

During the creation process of the contactless card 104, two cryptographic keys may be assigned uniquely per card. The cryptographic keys may comprise symmetric keys which may be used in both encryption and decryption of data. Triple DES (3DES) algorithm may be used by EMV and it is implemented by hardware in the contactless card 104. By using the key diversification process, one or more keys may be derived from a master key based upon uniquely identifiable information for each entity that requires a key.

In some examples, to overcome deficiencies of 3DES algorithms, which may be susceptible to vulnerabilities, a session key may be derived (such as a unique key per session) but rather than using the master key, the unique card-derived keys and the counter may be used as diversification data. For example, each time the contactless card 104 is used in operation, a different key may be used for creating the message authentication code (MAC) and for performing the encryption. This results in a triple layer of cryptography. The session keys may be generated by the one or more applets and derived by using the application transaction counter with one or more algorithms (as defined in EMV 4.3 Book 2 A1.3.1 Common Session Key Derivation).

Further, the increment for each card may be unique, and assigned either by personalization, or algorithmically assigned by some identifying information. For example, odd numbered cards may increment by 2 and even numbered cards may increment by 5. In some examples, the increment may also vary in sequential reads, such that one card may increment in sequence by 1, 3, 5, 2, 2, . . . repeating. The specific sequence or algorithmic sequence may be defined at personalization time, or from one or more processes derived from unique identifiers. This can make it harder for a replay attacker to generalize from a small number of card instances.

The authentication message may be delivered as the content of a text NDEF record in hexadecimal ASCII format. In another example, the NDEF record may be encoded in hexadecimal format.

Operations for the disclosed embodiments may be further described with reference to the following figures. Some of the figures may include a logic flow. Although such figures presented herein may include a particular logic flow, it can be appreciated that the logic flow merely provides an example of how the general functionality as described herein can be implemented. Further, a given logic flow does not necessarily have to be executed in the order presented unless otherwise indicated. Moreover, not all acts illustrated in a logic flow may be required in some implementations. In addition, the given logic flow may be implemented by a hardware element, a software element executed by a processor, or any combination thereof. The embodiments are not limited in this context.

Figure 5:
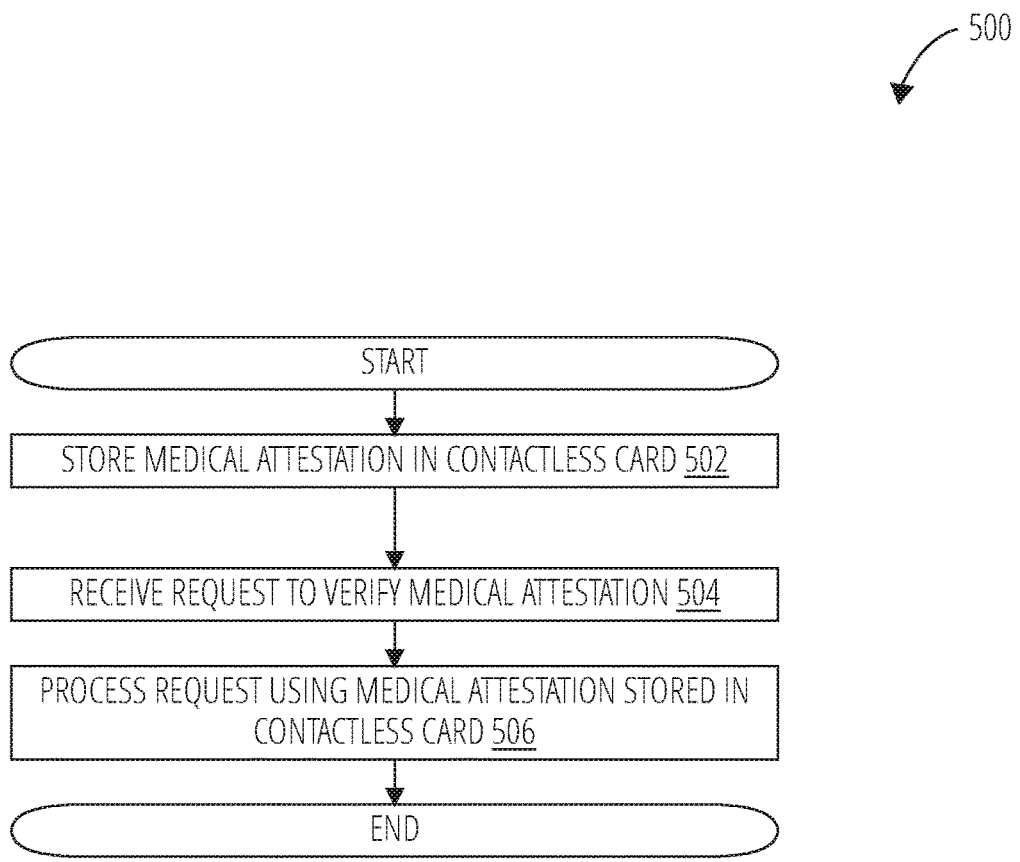
FIG. 5 illustrates a first logic flow.

FIG. 5 illustrates an embodiment of a logic flow 500. The logic flow 500 may be representative of some or all of the operations executed by one or more embodiments described herein. For example, the logic flow 500 may include some or all of the operations to use the contactless card 104 to provide secure verification of medical status using a contactless card. Embodiments are not limited in this context.

As shown, at block 502, the logic flow 500 includes storing a medical attestation 124 in a contactless card 104. Generally, as stated, an attestation 124 may relate to any PHI of a user. A digital signature 142 of the attestation 124 may be generated using a private key associated with the signing entity (e.g., a healthcare provider, etc.). The corresponding public key 146, the digital signature 142, and attestation 124 may then be stored in the contactless card 104. In some embodiments, a certificate chain associated with the digital signature is stored in the contactless card 104.

At block 504, the client application 122 and/or the applet 110 receives a request to verify the medical attestation 124 stored in the card 104. As stated, the request may be initiated by a user, an application, a device, or any other requesting entity. The request may specify a medical condition to be verified based on the medical attestation 124. At block 506, the applet 110 and/or the client application 122 processes the request using the medical attestation 124, public key 146, and digital signature 142. One or more associated operations to process the request are further described with reference to FIGS. 6 and 7. Generally, the applet 110 and/or the client application 122 may validate the certificate chain of the digital signature 142, decrypt the digital signature 142 using the public key 146, and compare the decrypted digital signature 142 to the medical attestation 124. If the comparison results in a match, the medical attestation 124 is verified. Similarly, based on the request, the applet 110 and/or the client application 122 may generate an attestation result. Generally, the attestation result is a response to the request based on the verified medical attestation 124. For example, if the request specifies to prove immunity to COVID-19, the applet 110 and/or the client application 122 may return a response indicating whether the person is immune to COVID-19 based on the attestation 124. Similarly, the applet 110 and/or the client application 122 may initiate performance of one or more operations based on the attestation result.

Figure 6:
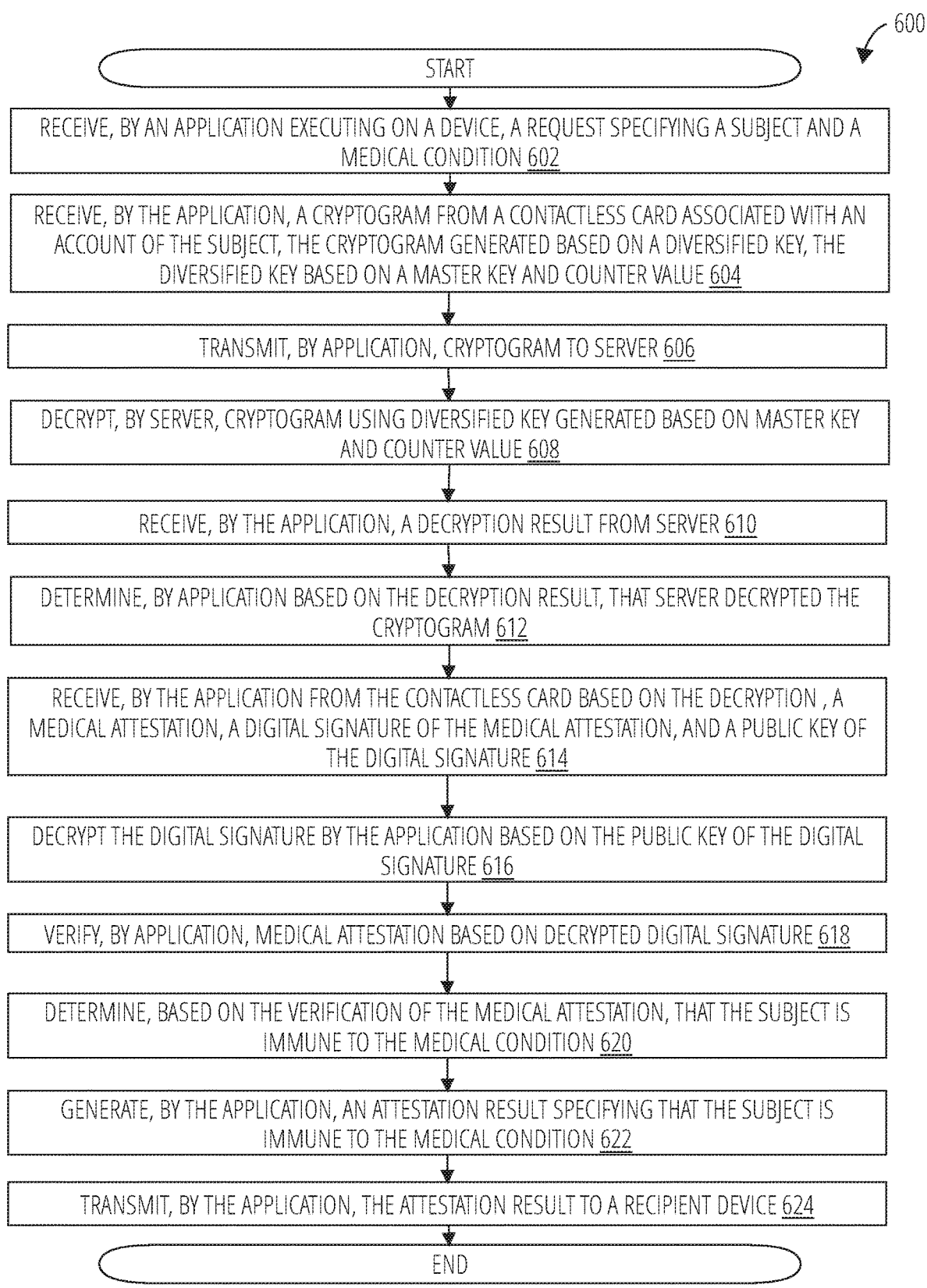
FIG. 6 illustrates a second logic flow.

FIG. 6 illustrates an embodiment of a logic flow 600. The logic flow 600 may be representative of some or all of the operations executed by one or more embodiments described herein. For example, the logic flow 600 may include some or all of the operations to verify medical status based on the attestation 124 stored in the contactless card 104. Embodiments are not limited in this context.

In block 602, logic flow 600 receives a request specifying a subject and a medical condition. For example, the client application 122 may receive a request specifying to verify that an authenticated account holder associated with a contactless card 104 prove immunity to COVID-19. For example, the client application 122 may include one or more selectable elements that allow the user to generate the request. In other examples, the request may be received from another application and/or another device. In block 604, logic flow 600 receives, by the application 122, a cryptogram from a contactless card associated with an account of the subject. The cryptogram may be generated based on the diversified key 116 and the customer ID 118. The diversified key 116 may be generated based on the counter 112 and the master key 114. The application 122 may transmit the cryptogram to the server 106 for verification at block 606.

In block 608, the server 106 decrypts the cryptogram by generating the diversified key from the current counter and the master key as described herein. At block 610, the application 122 receives a decryption result from the server 106. In block 612, the application 122 determines, based on the decryption result, that the server decrypted the cryptogram. In block 614, logic flow 600 receives, by the application 122 from the contactless card 104 based on the decryption result and/or based on the decryption of the cryptogram by the server, a medical attestation 124, a digital signature 142 of the medical attestation, and a public key 146 of the digital signature. In block 616, the application 122 decrypts the digital signature 142 based on the public key 146. In block 618, the application 122 verifies the medical attestation 124 based on the decrypted digital signature by comparing the decrypted digital signature to the medical attestation and determining the comparison results in a match. In block 620, the application 122 determines, based on the verification of the medical attestation 124, that the subject is immune to the medical condition. In block 622, the application 122 generates an attestation result specifying that the subject is immune to the medical condition. In block 624, the application 122 transmits the attestation result to a recipient device. Doing so may cause the recipient device to perform an operation, e.g., permit and/or deny access to public places.

Figure 7:
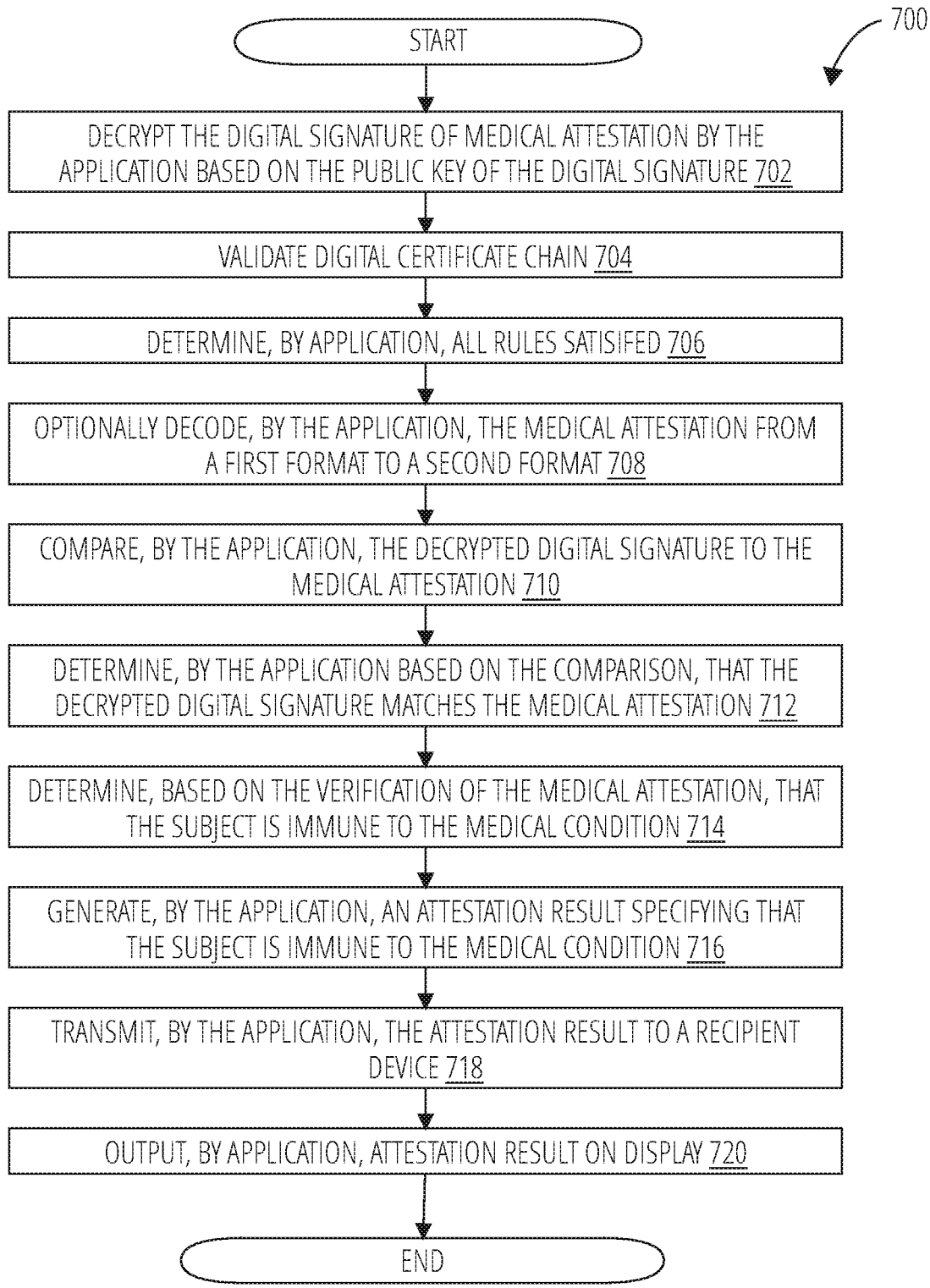
FIG. 7 illustrates a third logic flow.

FIG. 7 illustrates an embodiment of a logic flow 700. The logic flow 700 may be representative of some or all of the operations executed by one or more embodiments described herein. For example, the logic flow 700 may include some or all of the operations to process an attestation 124 stored in the contactless card 104. Embodiments are not limited in this context. Although discussed with reference to the client application 122, an applet 110 of the contactless card 104 may perform some or all of the operations of the logic flow 700.

In block 702, the client application 122 decrypts the digital signature 142 based on the public key 146. In block 704, the client application 122 verifies each certificate in a certificate chain associated with the digital signature 142. At block 706, the client application 122 determines that each of one or more rules are satisfied. For example, the rules may require that the digital signature 142 be signed by one or more predefined entities, e.g., a hospital, governmental agency, etc. If the digital signature 142 is signed by the one or more predefined entities (e.g. as reflected in the certificate chain), the client application 122 determines that these rules are satisfied. Similarly, decryption of the cryptogram by the server 106 may be another rule that is satisfied. In block 708, the client application 122 optionally decodes the medical attestation 124 from a first format to a second format, where the first and second formats are different data formats, different data types, etc.

At block 710, the client application 122 compares the medical attestation 124 to the decrypted digital signature 142. At block 712, the client application 122 determines that the decrypted digital signature matches the received medical attestation 124, thereby verifying the medical attestation 124. In block 714, the client application 122 determines, based on the verification of the medical attestation, that the subject is immune to the medical condition. In block 716, the client application 122 generates, by the application, an attestation result specifying that the subject is immune to the medical condition. In block 718, the client application 122 transmits the attestation result to a recipient device. At block 720, the client application 122 outputs the attestation result on a display of the device 102.

Figure 8:
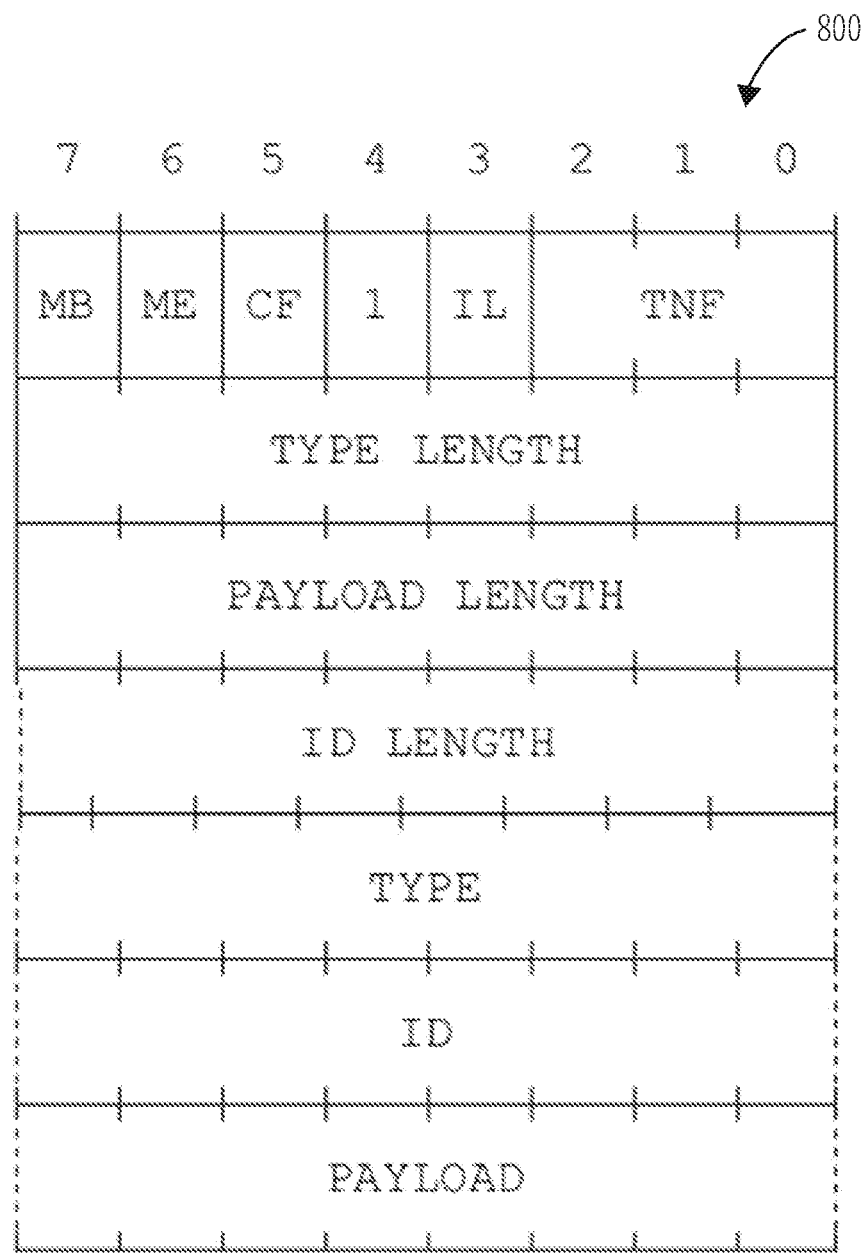
FIG. 8 illustrates a data structure in accordance with one embodiment.

FIG. 8 illustrates an NDEF short-record layout (SR=1) data structure 800 according to an example embodiment. One or more applets may be configured to encode the OTP as an NDEF type 4 well known type text tag. In some examples, NDEF messages may comprise one or more records. The applets may be configured to add one or more static tag records in addition to the OTP record. Exemplary tags include, without limitation, Tag type: well known type, text, encoding English (en); Applet ID: D2760000850104; Capabilities: read-only access; Encoding: the authentication message may be encoded as ASCII hex; type-length-value (TLV) data may be provided as a personalization parameter that may be used to generate the NDEF message. In an embodiment, the authentication template may comprise the first record, with a well-known index for providing the actual dynamic authentication data. In various embodiments, the payload of the data structure 800 may store a cryptogram (e.g., an encrypted customer ID 118), a medical attestation 124, a digital signature 142, and/or a public key 146.

Figure 9:
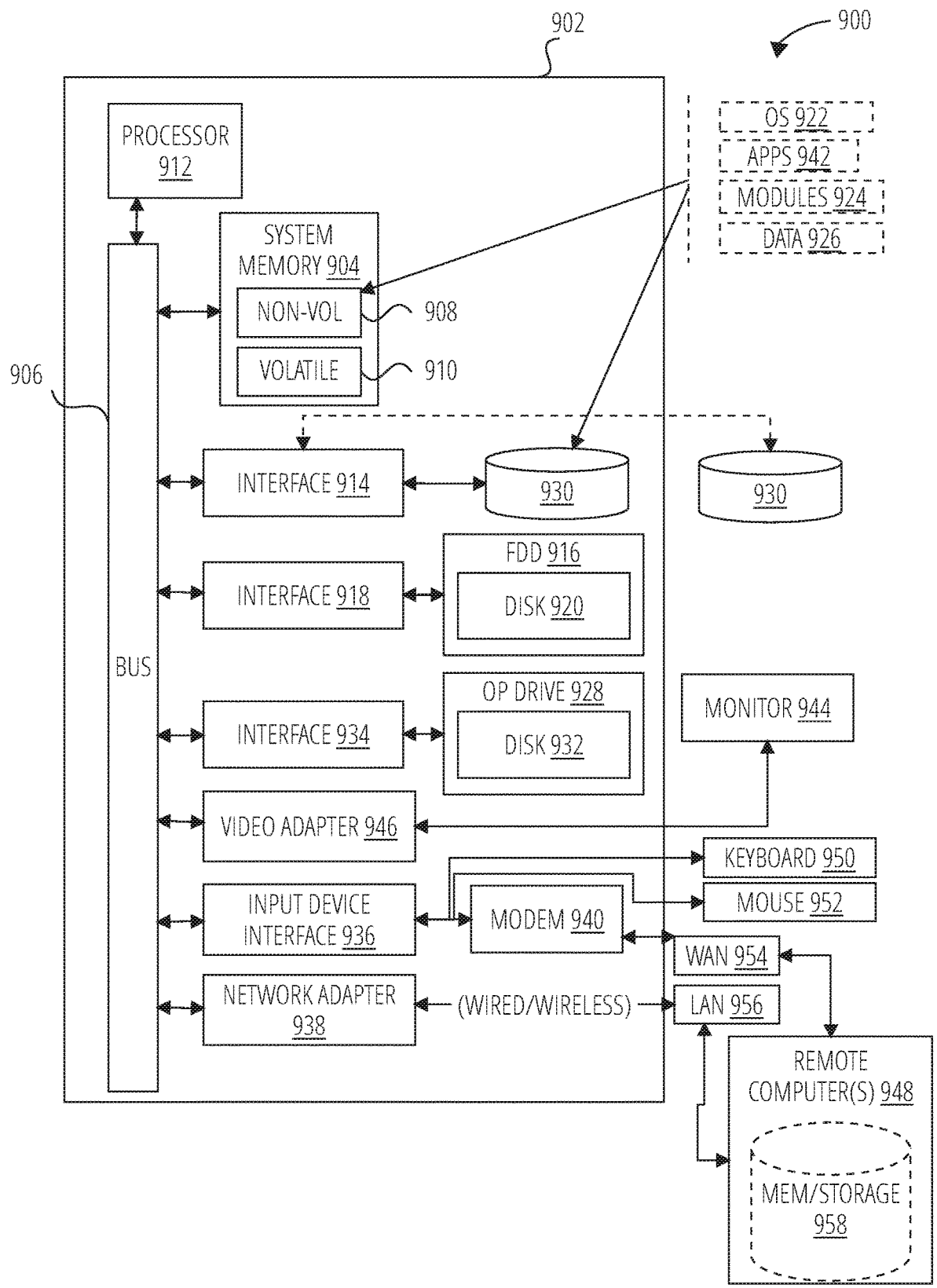
FIG. 9 illustrates a computer architecture in accordance with one embodiment.

FIG. 9 illustrates an embodiment of an exemplary computer architecture 900 comprising a computing system 902 that may be suitable for implementing various embodiments as previously described. In one embodiment, the computer architecture 900 may include or be implemented as part of computing architecture 100 or 200. In some embodiments, computing system 902 may be representative, for example, of the contactless card 104, computing devices 102, and server 106 of the systems 100-200. The embodiments are not limited in this context. More generally, the computing architecture 900 is configured to implement all logic, applications, systems, methods, apparatuses, and functionality described herein with reference to FIGS. 1A-8.

As used in this application, the terms "system" and "component" are intended to refer to a computer-related entity, either hardware, a combination of hardware and software, software, or software in execution, examples of which are provided by the exemplary computing computer architecture 900. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 900 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 100.

As shown in FIG. 9, the computing architecture 900 includes a processor 912, a system memory 904 and a system bus 906. The processor 912 can be any of various commercially available processors.

The system bus 906 provides an interface for system components including, but not limited to, the system memory 904 to the processor 912. The system bus 906 can be any of several types of bus structure that may further interconnect to a memory bus (with or without a memory controller), a peripheral bus, and a local bus using any of a variety of commercially available bus architectures. Interface adapters may connect to the system bus 908 via slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 900 may include or implement various articles of manufacture. An article of manufacture may include a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 904 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 9, the system memory 904 can include non-volatile 908 and/or volatile 910. A basic input/output system (BIOS) can be stored in the non-volatile 908.

The computer 902 may include various types of computer-readable storage media in the form of one or more lower speed memory units, including an internal (or external) hard disk drive 930, a magnetic disk drive 916 to read from or write to a removable magnetic disk 920, and an optical disk drive 928 to read from or write to a removable optical disk 932 (e.g., a CD-ROM or DVD). The hard disk drive 930, magnetic disk drive 916 and optical disk drive 928 can be connected to system bus 906 the by an HDD interface 914, and FDD interface 918 and an optical disk drive interface 934, respectively. The HDD interface 914 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and non-volatile 908, and volatile 910, including an operating system 922, one or more applications 942, other program modules 924, and program data 926. Example operating systems 922 include the Android® OS, iOS®, macOS®, Linux®, and Windows® operating systems. In one embodiment, the one or more applications 942, other program modules 924, and program data 926 can include, for example, the various applications and/or components of the systems 100-200, such as the applet 110, counter 112, master key 114, diversified key 116, customer ID 118, client application 122, attestation 124, encrypted customer ID 130, authentication application 134, account data 138, digital signature 142, decryption result 144, public key 146, encrypted customer ID 202, and decryption result 204.

A user can enter commands and information into the computer 902 through one or more wire/wireless input devices, for example, a keyboard 950 and a pointing device, such as a mouse 952. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, track pads, sensors, styluses, and the like. These and other input devices are often connected to the processor 912 through an input device interface 936 that is coupled to the system bus 906 but can be connected by other interfaces such as a parallel port, IEEE 1394 serial port, a game port, a USB port, an IR interface, and so forth.

A monitor 944 or other type of display device is also connected to the system bus 906 via an interface, such as a video adapter 946. The monitor 944 may be internal or external to the computer 902. In addition to the monitor 944, a computer typically includes other peripheral output devices, such as speakers, printers, and so forth.

The computer 902 may operate in a networked environment using logical connections via wire and/or wireless communications to one or more remote computers, such as a remote computer(s) 948. The remote computer(s) 948 can be a workstation, a server computer, a router, a personal computer, portable computer, microprocessor-based entertainment appliance, a peer device or other common network node, and typically includes many or all the elements described relative to the computer 902, although, for purposes of brevity, only a memory and/or storage device 958 is illustrated. The logical connections depicted include wire/wireless connectivity to a local area network 956 and/or larger networks, for example, a wide area network 954. Such LAN and WAN networking environments are commonplace in offices and companies, and facilitate enterprise-wide computer networks, such as intranets, all of which may connect to a global communications network, for example, the Internet.

When used in a local area network 956 networking environment, the computer 902 is connected to the local area network 956 through a wire and/or wireless communication network interface or network adapter 938. The network adapter 938 can facilitate wire and/or wireless communications to the local area network 956, which may also include a wireless access point disposed thereon for communicating with the wireless functionality of the network adapter 938.

When used in a wide area network 954 networking environment, the computer 902 can include a modem 940, or is connected to a communications server on the wide area network 954 or has other means for establishing communications over the wide area network 954, such as by way of the Internet. The modem 940, which can be internal or external and a wire and/or wireless device, connects to the system bus 906 via the input device interface 936. In a networked environment, program modules depicted relative to the computer 902, or portions thereof, can be stored in the remote memory and/or storage device 958. It will be appreciated that the network connections shown are exemplary and other means of establishing a communications link between the computers can be used.

The computer 902 is operable to communicate with wire and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.118 (a, b, g, n, etc.) to provide secure, reliable, fast wireless connectivity. A Wi-Fi network can be used to connect computers to each other, to the Internet, and to wire networks (which use IEEE 802.3-related media and functions).

The various elements of the devices as previously described with reference to FIGS. 1A-9 may include various hardware elements, software elements, or a combination of both. Examples of hardware elements may include devices, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. However, determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

What is claimed is:

1. A method, comprising:
    receiving, by an application executing on a device, a request specifying a person and whether the person is immune to a medical condition;
    receiving, by the application, encrypted data from a contactless card associated with the person;
    transmitting, by the application, the encrypted data to a server;
    determining, by the application based on a decryption result received from the server, that the server decrypted the encrypted data;
    receiving, by the application, based on the server decrypting the encrypted data, from the contactless card, a medical attestation, a digital signature of the medical attestation, and a public key of the digital signature;
    extracting, from the medical attestation, an encrypted customer identification (ID) and a counter value associated with the encrypted customer ID based on a rule to validate the encrypted customer ID of the medical attestation;
    transmitting the encrypted customer ID and the counter value to the server to validate the encrypted customer ID;
    determining, by the application based on a second decryption result received from the server, that the server decrypted the encrypted customer ID;
    verifying, by the application after successful decryption of the decrypted the encrypted customer ID by the server, the medical attestation based on the digital signature by determining that the digital signature is from an entity from a plurality of predefined entities approved to sign the medical attestation;
    determining, based on the verification of the medical attestation, that the person is not immune to the medical condition; and
    transmitting, by the application to a recipient device based on the determination that the person is not immune to the medical condition, an attestation result specifying that the person is not immune to the medical condition and to cause the recipient device to restrict access to an area.

2. The method of claim 1, wherein verifying the medical attestation further comprises:
    decrypting, by the application, the digital signature based on the public key of the digital signature; and
    verifying, by the application, the medical attestation based on the decrypted digital signature.

3. The method of claim 1, further comprising:
determining, by the application based on a first rule of a plurality of rules, a first predefined entity of a plurality of predefined entities approved to sign the medical attestation; and
determining, by the application, that a public key certificate chain for the digital signature includes a digital signature of the first predefined entity, wherein the verification of the medical attestation is based on the determination that the public key certificate chain for the digital signature includes the digital signature of the first predefined entity.

4. The method of claim 1, further comprising:
determining, by the application, that a public key certificate chain for the digital
signature does not include a digital signature of a first predefined entity of the plurality of predefined entities approved to sign the medical attestation, wherein the first predefined entity is specified by a first rule of a plurality of rules;
determining, by the application based on a second rule of the plurality of rules and the determination that the public key certificate chain does not include the digital signature of the first predefined entity, a second predefined entity of the plurality of predefined entities approved to sign the medical attestation; and
determining, by the application, that the public key certificate chain includes a first digital signature of the second predefined entity, wherein the verification of the
medical attestation is based on the determination that the public key certificate chain for the digital signature includes the digital signature of the second predefined entity.

5. The method of claim 1, further comprising:
decoding, by the application, the medical attestation from a first data type to a second data type, the first data type different than the second data type.

6. The method of claim 1, wherein the medical attestation comprises: (i) a unique customer identifier assigned to the person, (ii) a date of the medical attestation, (iii) the medical attestation of the person, and (iv) a second encrypted data generated by the contactless card, wherein the attestation result further specifies the date of the medical attestation.

7. The method of claim 6, further comprising:
transmitting, by the application, the second encrypted data to the server; receiving, by the application from the server, a decryption result of the second
encrypted data; and
determining, by the application based on the decryption result of the second encrypted data, that the server decrypted the second encrypted data, wherein the application further determines that the person is not immune to the medical condition based on the determination that the server decrypted the second encrypted data.

8. A non-transitory computer-readable storage medium, the computer-readable storage medium including instructions that when executed by a processor, cause the processor to:
receive a request specifying a person and whether the person is immune to a medical condition;
receive encrypted data from a contactless card associated with the person; transmit the encrypted data to a server;
determine, based on a decryption result received from the server, that the server decrypted the encrypted data;
receive, from the contactless card, based on the server decrypting the encrypted data, a medical attestation, a digital signature of the medical attestation, and a public key of the digital signature;
extract, from the medical attestation, an encrypted customer identification (ID) and a counter value associated with the encrypted customer ID based on a rule to validate the encrypted customer ID of the medical attestation;
transmit the encrypted customer ID and the counter value to the server to validate the encrypted customer ID;
determine, based on a second decryption result received from the server, that the server decrypted the encrypted customer ID;
verify, after successful decryption of the decrypted the encrypted customer ID by the server, the medical attestation based on the digital signature by a determination that the digital signature is from an entity from a plurality of predefined entities approved to sign the medical attestation;
determine, based on the verification of the medical attestation, that the person is not immune to the medical condition; and
transmit, to a recipient device based on the determination that the person is not immune to the medical condition, an attestation result specifying that the person is not immune to the medical condition to cause the recipient device to restrict access to an area.

9. The computer-readable storage medium of claim 8, wherein the instructions to verify the medical attestation further comprise instructions that when executed by the processor cause the processor to:
decrypt the digital signature based on the public key of the digital signature; and verify the medical attestation based on the decrypted digital signature.

10. The computer-readable storage medium of claim 8, wherein the instructions further cause the processor to:
determine, based on a first rule of a plurality of rules, a first predefined entity of the plurality of predefined entities approved to sign the medical attestation; and
determine that a public key certificate chain for the digital signature includes a digital signature of the first predefined entity, wherein the verification of the medical attestation is based on the determination that the public key certificate chain for the digital signature includes the digital signature of the first predefined entity.

11. The computer-readable storage medium of claim 8, wherein the instructions further cause the processor to:
determine that a public key certificate chain for the digital signature does not include a digital signature of a first predefined entity of a plurality of predefined entities approved to sign the medical attestation, wherein the first predefined entity is specified by a first rule of a plurality of rules;
determine, based on a second rule of the plurality of rules and the determination that the public key certificate chain does not include the digital signature of the first predefined entity, a second predefined entity of the plurality of predefined entities approved to sign the medical attestation; and
determine that the public key certificate chain includes a first digital signature of the second predefined entity, wherein the verification of the medical attestation is based on the determination that the public key certificate chain for the digital signature includes the digital signature of the second predefined entity.

12. The computer-readable storage medium of claim 8, wherein the instructions further configure the computer to:

decode the medical attestation from a first data type to a second data type, the first data type different than the second data type.

13. The computer-readable storage medium of claim 8, wherein the medical attestation comprises: (i) a unique customer identifier assigned to the person, (ii) a date of the medical attestation, (iii) the medical attestation of the person, and (iv) a second encrypted data generated by the contactless card, wherein the attestation result further specifies the date of the medical attestation.

14. The computer-readable storage medium of claim 13, wherein the instructions further cause the processor to:
   transmit the second encrypted data to the server;
   receive, from the server, a decryption result of the second encrypted data; and
   determine, based on the decryption result of the second encrypted data, that the server decrypted the second encrypted data, wherein the processor further determines that the person is not immune to the medical condition based on the determination that the server decrypted the second encrypted data.

15. A computing apparatus comprising:
   a processor; and
   a memory storing instructions that, when executed by the processor, cause the processor to:
      receive a request specifying a person and whether the person is immune to a medical condition;
      receive encrypted data from a contactless card associated with the person;
transmit the encrypted data to a server;
      determine, based on a decryption result received from the server, that the server decrypted the encrypted data;
      receive, from the contactless card, based on the server decrypting the encrypted data, a medical attestation, a digital signature of the medical attestation, and a public key of the digital signature;
      extracting, from the medical attestation, an encrypted customer identification (ID) and a counter value associated with the encrypted customer ID based on a rule to validate the encrypted customer ID of the medical attestation;
      transmit the encrypted customer ID and the counter value to the server to validate the encrypted customer ID;
      determine, based on a second decryption result received from the server, that the server decrypted the encrypted customer ID;
      verify, after successful decryption of the decrypted the encrypted customer ID by the server, the medical attestation based on the digital signature according to a determination that the digital signature is from an entity from a plurality of predefined entities approved to sign the medical attestation;
      determine, based on the verification of the medical attestation, that the person is not immune to the medical condition; and
      transmit, to a recipient device based on the determination that the person is not immune to the medical condition, an attestation result specifying that the person is not immune to the medical condition to cause the recipient device to restrict access to an area.

16. The computing apparatus of claim 15, wherein the instructions to verify the medical attestation further comprise instructions that when executed by the processor cause the processor to:
   decrypt the digital signature based on the public key of the digital signature; and verify the medical attestation based on the decrypted digital signature.

17. The computing apparatus of claim 15, wherein the instructions further cause the processor to:
   determine, based on a first rule of a plurality of rules, a first predefined entity of a plurality of predefined entities approved to sign the medical attestation; and
   determine that a public key certificate chain for the digital signature includes a digital signature of the first predefined entity, wherein the verification of the medical attestation is based on the determination that the public key certificate chain for the digital signature includes the digital signature of the first predefined entity.

18. The computing apparatus of claim 15, wherein the instructions further cause the processor to:
   determine that a public key certificate chain for the digital signature does not include a digital signature of a first predefined entity of the plurality of predefined entities approved to sign the medical attestation, wherein the first predefined entity is specified by a first rule of a plurality of rules;
   determine, based on a second rule of the plurality of rules and the determination that the public key certificate chain does not include the digital signature of the first predefined entity, a second predefined entity of the plurality of predefined entities approved to sign the medical attestation; and
   determine that the public key certificate chain includes a first digital signature of the second predefined entity, wherein the verification of the medical attestation is based on the determination that the public key certificate chain for the digital signature includes the digital signature of the second predefined entity;
   instructions further cause the processor to:
   decode the medical attestation from a first data type to a second data type, the first data type different than the second data type.

19. The computing apparatus of claim 15, wherein the medical attestation comprises: (i) a unique customer identifier assigned to the person, (ii) a date of the medical attestation, (iii) the medical attestation of the person, and (iv) a second encrypted data generated by the contactless card, wherein the attestation result further specifies the date of the medical attestation.

* * * * *

UNITED STATES PATENT AND TRADEMARK OFFICE
CERTIFICATE OF CORRECTION

| | | |
|---|---|---|
| PATENT NO. | : 12,046,336 B2 | Page 1 of 1 |
| APPLICATION NO. | : 17/948401 | |
| DATED | : July 23, 2024 | |
| INVENTOR(S) | : Kevin Osborn et al. | |

It is certified that error appears in the above-identified patent and that said Letters Patent is hereby corrected as shown below:

In the Claims

Claim 15, Column 25, Line 38, in "extracting, from the medical attestation", replace "extracting" with "extract".

Signed and Sealed this
Seventeenth Day of December, 2024

Derrick Brent
*Acting Director of the United States Patent and Trademark Office*